United States Patent
Stack

(10) Patent No.: US 11,839,284 B2
(45) Date of Patent: Dec. 12, 2023

(54) BODY HAIR REMOVAL PAD FOR DEFIBRILLATOR USAGE

(71) Applicant: Julia Stack, Spring Hill, FL (US)

(72) Inventor: Julia Stack, Spring Hill, FL (US)

(*) Notice: Subject to any disclaimer, the term of this patent is extended or adjusted under 35 U.S.C. 154(b) by 0 days.

(21) Appl. No.: 16/912,708

(22) Filed: Jun. 26, 2020

(65) Prior Publication Data

US 2020/0405032 A1  Dec. 31, 2020

Related U.S. Application Data

(60) Provisional application No. 62/866,417, filed on Jun. 25, 2019.

(51) Int. Cl.
*A45D 26/00* (2006.01)
*A61N 1/39* (2006.01)

(52) U.S. Cl.
CPC .... *A45D 26/0019* (2013.01); *A45D 2026/008* (2013.01); *A61N 1/39* (2013.01)

(58) Field of Classification Search
CPC ............... A45D 26/00; A45D 26/0014; A45D 26/0019; A45D 26/008; A61N 1/39–3993
See application file for complete search history.

(56) References Cited

U.S. PATENT DOCUMENTS

| | | | | |
|---|---|---|---|---|
| 4,752,148 A | * | 6/1988 | Mann | A45D 34/041 401/195 |
| 2005/0070963 A1 | * | 3/2005 | Wilson | A45D 26/0019 607/5 |
| 2012/0029530 A1 | * | 2/2012 | Gunstream | A45D 26/0019 606/134 |
| 2012/0143214 A1 | * | 6/2012 | Iwegbu | A45D 26/00 606/133 |
| 2013/0150867 A1 | * | 6/2013 | Atteia | A45D 26/0019 606/133 |
| 2017/0202334 A1 | * | 7/2017 | Power | A61N 1/18 |

* cited by examiner

*Primary Examiner* — Todd J Scherbel
(74) *Attorney, Agent, or Firm* — Charlena Thorpe, Esq.; Incorporating Innovation LLC

(57) ABSTRACT

Implementations of a body hair removal pad for defibrillator usage ("defibrillator hair removal pad") are provided. In some implementations, the defibrillator hair removal pad comprises a base (or base layer) and an adhesive layer.
In some implementations, a method for using the defibrillator hair removal pad comprises positioning the adhesive layer on the skin of a heart attack victim and pulling the adhesive layer from the skin of the heart attack victim with the adhesive layer stuck to the body hair on the skin.

7 Claims, 14 Drawing Sheets

BODY HAIR REMOVAL PAD FOR DEFIBRILLATOR USAGE

CROSS REFERENCE TO RELATED APPLICATION

This application claims the benefit of U.S. Patent Application Ser. No. 62/866,417, which was filed on Jun. 25, 2019, and is incorporated herein by reference in its entirety.

TECHNICAL FIELD

This disclosure relates to implementations of a body hair removal pad for defibrillator usage.

BACKGROUND

Automated external defibrillators (AEDs), and other similar modern defibrillators, are attached to a heart attack victim for emergency treatment using specialized adhesive electrode pads. The replaceable one-use per-patient adhesive electrode pads are stuck to the skin on the victim's chest to allow the AED to administer life-saving electrical shocks to the victim's heart. Therefore, the adhesive electrode pads have to securely stick to the heart attack victim's skin for the AED to work properly to save the victim's life.

However, body hair at the attachment points on the victim's chest prevents the adhesive electrode pads from securely sticking to the skin as required. Therefore, such body hair has to be removed prior to sticking the adhesive electrode pads to the victim's chest.

An existing way to remove such body hair is to use an extra set of the adhesive electrode pads to pull off the body hair before using a second set of the adhesive electrode pads to attach the AED to the victim. However, this existing way is costly and wasteful since it uses an extra set of the specialized adhesive electrode pads that cannot be used afterward to attach the AED and have to be thrown away. Also, this existing way usually does not clear a sufficient area, i.e. length and/or width, of the body hair on the first attempt since a larger area of hair than the size of the pad has to be removed. As a result, yet another extra set of the adhesive electrode pads may need to be used before the AED can be attached to the victim, which also further delays the life-saving AED usage.

Furthermore, this existing way can be difficult and time delaying because the adhesive electrode pad does not include design features to allow the pad to be quickly and easily pulled to remove the hair. Moreover, safety is compromised by use of the AED adhesive electrode pads in this manner, because the AED is rendered unusable until the adhesive electrode pads are replaced.

Another existing way to remove such body hair is to use a razor to shave off the body hair before attaching the AED to the victim with the adhesive electrode pads. However, this existing way poses a risk of causing injury and creating a biological hazard while trying to shave the body hair to quickly attach the AED to a suffering heart attack victim.

DETAILED DESCRIPTION

Figure 1A:
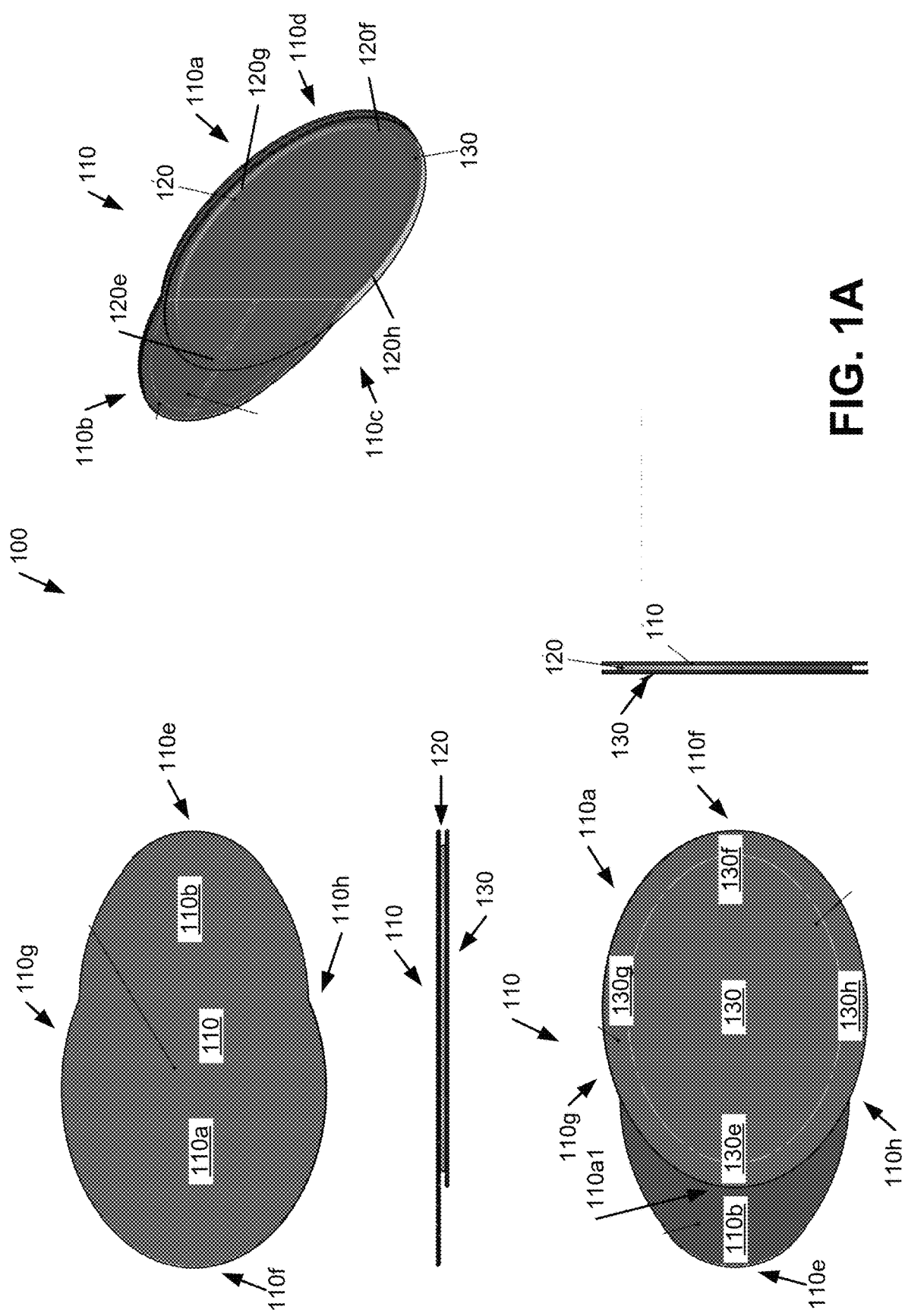
FIGS. 1A and 1B illustrate various views of an implementation of an example body hair removal pad for defibrillator usage according to the present disclosure.

Implementations of a body hair removal pad for defibrillator usage ("defibrillator hair removal pad") are provided. In some implementations, the defibrillator hair removal pad comprises a base (or base layer) and an adhesive layer. In some implementations, the defibrillator hair removal pad further comprises an adhesive layer covering.

In some implementations, the defibrillator hair removal pad may further comprise a thermal enclosure bag configured to enclose the defibrillator hair removal pad.

In some implementations, the defibrillator hair removal pad is configured to adhere to and remove body hair from the skin of a heart attack victim's chest. For example, in some implementations, the defibrillator hair removal pad is configured to stick to and pull the body hair from the skin of the heart attack victim's chest.

In some implementations, the defibrillator hair removal pad is configured to remove the body hair to allow the unobstructed and secure sticking of adhesive electrode pads of an automated external defibrillator (AED) or similar defibrillator device to the skin of the heart attack victim's chest.

In some implementations, the defibrillator hair removal pad is configured to allow the unobstructed and secure sticking of the adhesive electrode pads so that the AED can be properly used to administer life-saving electrical impulses to the victim's heart.

In some implementations, the defibrillator hair removal pad is configured to be quickly and easily pulled to remove the body hair from the skin of a heart attack victim's chest.

In some implementations, the defibrillator hair removal pad is configured to remove a surface area, i.e. length, width, and/or shape, of the body hair that is larger than the surface area of the AED adhesive electrode pad. In some implementations, the defibrillator hair removal pad is configured to remove such larger surface area of the body hair so that the entire contact surface of the AED adhesive electrode pads can be fully and easily stuck to the skin of a heart attack victim's chest.

In some implementations, the defibrillator hair removal pad is configured to be sufficiently durable to allow the defibrillator hair removal pad to be quickly and easily pulled to remove the body hair from the skin of a heart attack victim without tearing or otherwise damaging the defibrillator hair removal pad.

In some implementations, the defibrillator hair removal pad is configured to provide a sufficient amount of adhesive to quickly, easily, and sufficiently adhere to and remove the body hair from the skin of a heart attack victim.

In some implementations, the defibrillator hair removal pad is configured to be used to remove the body hair from the skin of a heart attack victim without causing a risk of injury or of creating a biological hazard, e.g. in contrast to using a razor. For example, in some implementations, the defibrillator hair removal pad is configured to be used to remove the body hair from the skin of a heart attack victim without causing such risk to the heart attack victim or the AED user, such as a first responder or other concerned person.

In some implementations, a method for using the defibrillator hair removal pad comprises positioning the adhesive layer of the defibrillator hair removal pad on body hair on the skin of a heart attack victim.

In some implementations, the method comprises pulling the adhesive layer from the skin of a heart attack victim with the adhesive layer stuck to the body hair on the skin of the heart attack victim.

In some implementations, the method further comprises removing the adhesive layer covering from the adhesive layer of the defibrillator hair removal pad before positioning the adhesive layer.

Figure 1B:
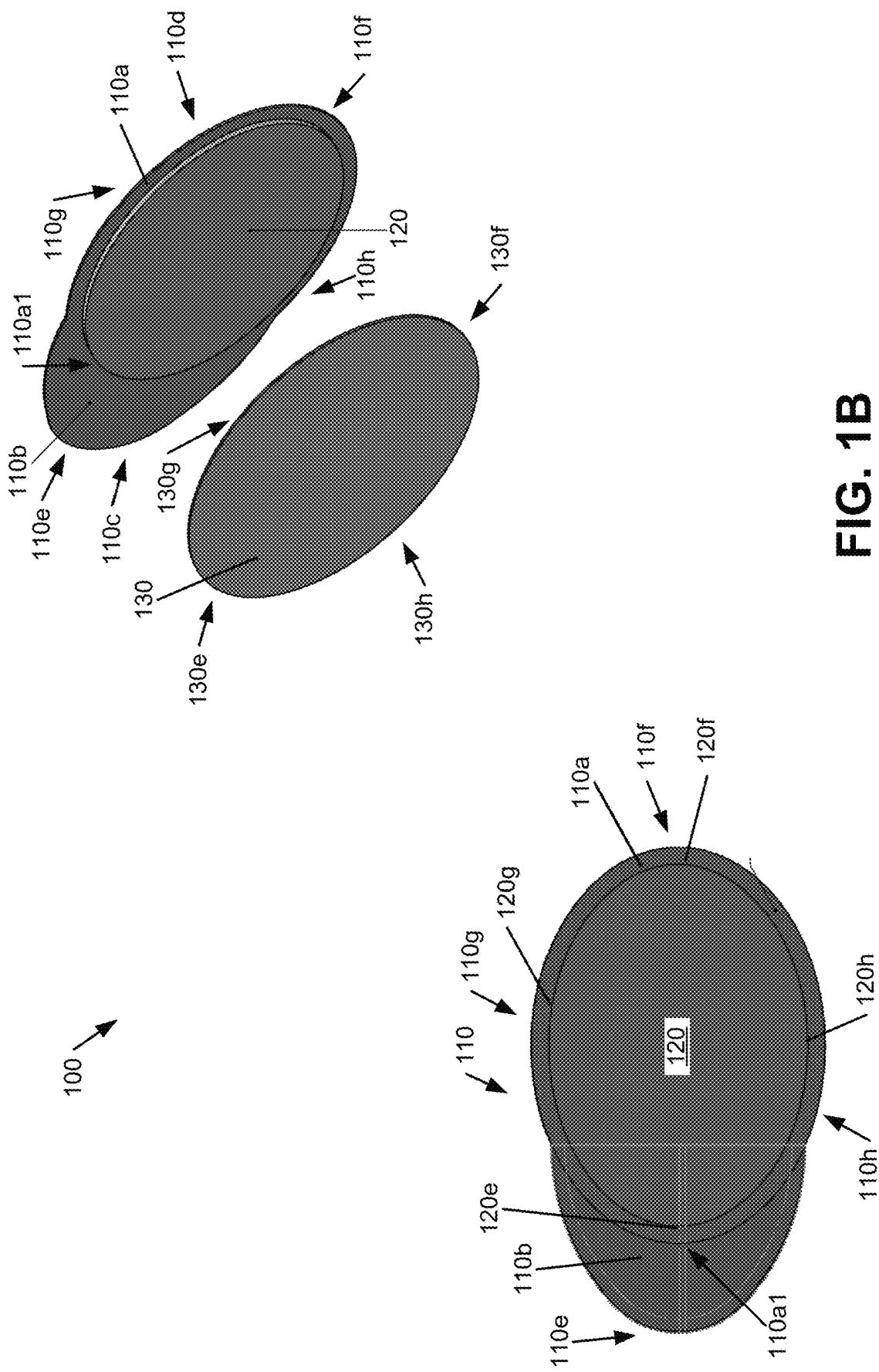

FIGS. 1A and 1B illustrate various views of an implementation of an example body hair removal pad for defibrillator usage ("defibrillator hair removal pad") 100 according to the present disclosure.

As shown in FIG. 1A, in some implementations, the defibrillator hair removal pad 100 comprises a base (or base layer) 110, an adhesive layer 120, and an adhesive layer covering 130.

In some implementations, the adhesive layer 120 is securely attached to the base 110. In some implementations, the adhesive layer covering 130 is removably attached to the adhesive layer 120 opposite the attachment of the adhesive layer 120 to the base 110.

As shown in FIG. 1A, in some implementations, the base 110 comprises a main portion 110a and a pull tab portion 110b. As shown in FIG. 1B, in some implementations, the base 110 comprises a front side 110c, a back side 110d, a left side 110e, a right side 110f, a top side 110g, and a bottom side 110h.

As shown in FIG. 1A, in some implementations, the base 110 is flat. For example, in some implementations, the depth of the base 110 between the front side 110c and the back side 110d is narrow.

In some implementations, the base 110 is substantially and/or semi oval shaped. For example, in some implementations, the base 110 is curved around the edge of the base 110 along the top side 110g, the left side 110e, the bottom side 110h, and the right side 110f. Furthermore, in some implementations, the length of the base 110 between the left side 110e and the right side 110f is greater than the width of the base 110 between the top side 110g and the bottom side 110h.

In some implementations, the base 110 may have any other suitable shape and/or dimensional proportions.

As shown in FIG. 1B, in some implementations, the main portion 110a comprises a left side 110a1. In some implementations, the extents of the main portion 110a are defined by the main portion left side 110a1, the base right side 110f, the base top side 110g, and the base bottom side 110h.

In some implementations, the main portion 110a of the base 110 is oval shaped, similar to as described above for the shape of the base 110. For example, in some implementations, the main portion 110a is curved around the edge of the main portion 110a along the base top side 110g, the main portion left side 110a1, the base bottom side 110h, and the base right side 110f. Furthermore, in some implementations, the length of the main portion 110a between the main portion left side 110a1 and the base right side 110f is greater than the width of the main portion 110a between the base top side 110g and the base bottom side 110h.

In some implementations, the main portion 110a may have any other suitable shape.

As shown in FIG. 1B, in some implementations, the extents of the pull tab portion 110b are defined by the base left side 110e, the main portion left side 110a1, the base top side 110g, and the base bottom side 110h.

In some implementations, the pull tab portion 110b is semi and/or partially oval shaped with respect to the defining sides 110g, 110e, 110h, 110a1 of the pull tab portion 110b. In some implementations, the pull tab portion 110b may have any other suitable shape.

In some implementations, the pull tab portion 110b may further comprise one or more pull tab openings (not shown) extending through the pull tab portion 110b. In some implementations, the one or more pull tab openings are configured to allow a user of the defibrillator hair removal pad 100 to insert one or more of the user's fingers into and/or through the pull tab opening(s).

In some implementations, the one or more pull tab openings are configured to thereby allow the user of the defibrillator hair removal pad 100 to get a better and/or firmer grip on the defibrillator hair removal pad 100 by the pull tab portion 110b. For example, in some implementations, the one or more pull tab openings are configured to allow the user of the defibrillator hair removal pad 100 to get a better and/or firmer grip to pull the defibrillator hair removal pad 100 by the pull tab portion 110b to remove body hair from the skin of a heart attack victim.

As shown in FIG. 1B, in some implementations, the base 110 is configured to allow the adhesive layer 120 to be securely attached to the base 110. In some implementations, the base 110 is configured to allow the adhesive layer 120 to be securely attached on the front side 110c of the base 110. In some implementations, the base 110 is configured to allow the adhesive layer 120 to be securely attached to the main portion 110a of the base 110.

In some implementations, the base 110 is configured to allow the adhesive layer 120 to be securely attached to the main portion 110a on the front side 110c of the base 110. In some implementations, the base 110 may be configured to allow the adhesive layer 120 to be securely attached to and/or on any other suitable part of the base 110.

In some implementations, the base 110 is configured to allow the adhesive layer 120 to be securely attached to the main portion 110a of the base 110 and not attached to the pull tab portion 110b of the base 110. That is, in some implementations, the base 110 is configured so that the adhesive layer 120 does not attach to the pull tab portion 110b of the base 110 but does securely attach to the main portion 110a of the base 110.

In some implementations, the base 110 is configured to allow the adhesive layer 120 to be securely attached to the base 110 so that the adhesive layer 120 can be stuck to body hair on the skin of a heart attack victim. For example, in some implementations, the base 110 is configured to allow the adhesive layer 120 to be securely attached to the base 110 so that the adhesive layer 120 can be stuck to body hair on the skin of a heart attack victim's chest.

In some implementations, the base 110 is configured to allow the adhesive layer 120 to be securely attached so that the adhesive layer 120 can be pulled by the base 110 to remove the body hair from the skin of the heart attack victim. For example, in some implementations, the base 110 is configured to allow the adhesive layer 120 to be securely attached to the base 110 so that the adhesive layer 120 can be pulled by the base 110 to remove the body hair from the skin of a heart attack victim's chest.

In some implementations, the base 110 is configured to position the adhesive layer 120 while securely attached to the base 110. In some implementations, the base 110 is configured to position the adhesive layer 120 on body hair on the skin of a heart attack victim. For example, in some implementations, the base 110 is configured to position the adhesive layer 120 on body hair on the skin of a heart attack victim's chest.

In some implementations, the base 110 is configured to position the adhesive layer 120 on the body hair on the skin of a heart attack victim to remove the body hair from the skin. For example, in some implementations, the base 110 is configured to position the adhesive layer 120 on the body hair of a heart attack victim to remove the body hair from the skin of the heart attack victim's chest.

In some implementations, the base 110 is configured to be pulled by the pull tab portion 110b of the base 110. In some implementations, the base 110 is configured to be pulled by the pull tab portion 110b to thereby pull the adhesive layer 120 while securely attached to the base 110.

In some implementations, the base 110 is configured to be pulled by the pull tab portion 110b to thereby pull the adhesive layer 120 to remove body hair from the skin of a heart attack victim. For example, in some implementations, the base 110 is configured to be pulled by the pull tab portion 110b to thereby pull the adhesive layer 120 to remove body hair from the skin of a heart attack victim's chest.

In some implementations, the base 110 may be composed of a plastic material. For example, in some implementations, the base 110 may be composed of a durable multi-fiber plastic sheet material, such as Tyvek®. In some implementations, the base 110 may be composed of any other suitable material.

In some implementations, the base 110 is composed of a material that is more durable than existing hair removal strips.

In some implementations, the base 110 is composed of a non-woven material.

In some implementations, the base 110 may be composed of a material that is similar to the material of the adhesive electrode pad of an automated external defibrillator (AED) or similar defibrillator device.

As shown in FIG. 1B, in some implementations, the adhesive layer 120 comprises a left side 120e, a right side 120f, a top side 120g, and a bottom side 120h.

In some implementations, the adhesive layer 120 comprises a layer of any suitable adhesive, such as a substance with suitable adhesive characteristics for effectively removing body hair as described herein. For example, in some implementations, the adhesive layer 120 may comprise a wax substance.

In some implementations, the extents of the adhesive layer 120 are defined by the left side 120e, the right side 120f, the top side 120g, and the bottom side 120h.

In some implementations, the adhesive layer 120 is oval shaped, the same or similar to the shape of the main portion 110a of the base 110 described above. For example, in some implementations, the adhesive layer 120 is curved around the edge of the adhesive layer 120 along the top side 120g, the left side 120e, the bottom side 120h, and the right side 120f. Furthermore, in some implementations, the length of the adhesive layer 120 between the left side 120e and the right side 120f is greater than the width of the adhesive layer 120 between the top side 120g and the bottom side 120h.

In some implementations, the adhesive layer 120 may have any other suitable shape and/or dimensional proportions.

In some implementations, the adhesive layer 120 is sized, i.e. in length and/or width, to extend over all or most of the extents of the main portion 110a, which are defined by the sides 110a1, 110f, 110g, 110h as described above.

In some implementations, the adhesive layer 120 may be sized to extend over any other suitable portion of the extents of the main portion 110a, as described below.

In some implementations, the adhesive layer 120 is configured to securely attach on the front side 110c of the base 110. In some implementations, the adhesive layer 120 is configured to securely attach to the main portion 110a of the base 110.

In some implementations, the adhesive layer 120 is configured to securely attach to the main portion 110a on the front side 110c of the base 110. In some implementations, the adhesive layer 120 is configured to securely attach to and/or on any other suitable part of the base 110.

In some implementations, the adhesive layer 120 is configured to securely attach to the main portion 110a of the base 110 and not attach to the pull tab portion 110b of the base 110.

In some implementations, the adhesive layer 120 is configured to securely attach to the base 110 so that the adhesive layer 120 can be stuck to body hair on the skin of a heart attack victim. For example, in some implementations, the adhesive layer 120 is configured to securely attach to the base 110 so that the adhesive layer 120 can be stuck to body hair on the skin of a heart attack victim's chest.

In some implementations, the adhesive layer 120 is configured to securely attach to the base 110 so that the adhesive layer 120 can be pulled by the base 110 to remove the body hair from the skin of the heart attack victim. For example, in some implementations, the adhesive layer 120 is configured to securely attach to the base 110 so that the adhesive layer 120 can be pulled by the base 110 to remove the body hair from the skin of a heart attack victim's chest.

In some implementations, the adhesive layer 120 is configured to be positioned by the base 110. In some implementations, the adhesive layer 120 is configured to be positioned by the base 110 on body hair on the skin of a heart attack victim. For example, in some implementations, the adhesive layer 120 is configured to be positioned by the base 110 on body hair on the skin of a heart attack victim's chest.

In some implementations, the adhesive layer 120 is configured to be positioned by the base 110 on the body hair on the skin of a heart attack victim to remove the body hair from the skin. For example, in some implementations, the adhesive layer 120 is configured to be positioned by the base 110 on the body hair of a heart attack victim to remove the body hair from the skin of the heart attack victim's chest.

In some implementations, the adhesive layer 120, securely attached to the base 110, is configured to be pulled using the pull tab portion 110b of the base 110.

In some implementations, the adhesive layer 120, securely attached to the base 110, is configured to be pulled to remove body hair from the skin of a heart attack victim. For example, in some implementations, the adhesive layer 120, securely attached to the base 110, is configured to be pulled to remove body hair from the skin of a heart attack victim's chest.

In some implementations, the adhesive layer 120 is configured to be thicker than the adhesive on existing hair removal strips. In some implementations, the adhesive layer 120 is configured to be more durable than the adhesive on existing hair removal strips.

In some implementations, the adhesive layer 120 is composed of a substance with suitable adhesive characteristics for securely attaching to the base 110 as described herein. In some implementations, the adhesive layer 120 is composed of a substance with suitable adhesive characteristics for effectively sticking to and removing body hair as described herein.

For example, in some implementations, the adhesive layer 120 is composed of a pressure sensitive adhesive (PSA) or similar substance. In some implementations, the adhesive layer 120 is composed of a rubber type adhesive or similar substance. In some implementations, the adhesive layer 120 is composed of any other suitable substance with such suitable adhesive characteristics.

As shown in FIG. 1B, in some implementations, the adhesive layer covering 130 comprises a left side 130e, a right side 130f, a top side 130g, and a bottom side 130h.

In some implementations, the extents of the adhesive layer covering 130 are defined by the left side 130e, the right side 130f, the top side 130g, and the bottom side 130h.

In some implementations, the adhesive layer covering 130 is oval shaped, the same or similar to the shape of the adhesive layer 120 described above. For example, in some implementations, the adhesive layer covering 130 is curved around the edge of the adhesive layer covering 130 along the top side 130g, the left side 130e, the bottom side 130h, and the right side 130f. Furthermore, in some implementations, the length of the adhesive layer covering 130 between the left side 130e and the right side 130f is greater than the width of the adhesive layer covering 130 between the top side 130g and the bottom side 130h.

In some implementations, the adhesive layer covering 130 may have any other suitable shape and/or dimensional proportions.

As shown in FIG. 1A, in some implementations, the adhesive layer covering 130 is sized, i.e. in length and/or width, to extend over at least all or most of the extents of the adhesive layer 120, which are defined by the sides 120e, 120f, 120g, 120h of the adhesive layer 120 as described above.

In some implementations, the adhesive layer covering 130 is sized to extend over and beyond all of the extents of the adhesive layer 120 adjacent to one or more sides 130e, 130f, 130g, 130h of the adhesive layer covering 130, as described below.

In some implementations, the adhesive layer covering 130 is sized to extend over any other suitable portion of the extents of the adhesive layer 120.

In some implementations, the adhesive layer covering 130 is configured to removably attach to the adhesive layer 120. In some implementations, the adhesive layer covering 130 is configured to removably attach to the adhesive layer 120 opposite the attachment of the adhesive layer 120 to the main portion 110a of the base 110. In some implementations, the adhesive layer covering 130 is configured to removably attach to the adhesive layer 120 opposite the attachment of the adhesive layer 120 to the main portion 110a on the front side 110c of the base 110.

In some implementations, the adhesive layer covering 130 is configured to removably attach to any other suitable location on the adhesive layer 120.

In some implementations, the adhesive layer covering 130 is configured to cover the adhesive layer 120. In some implementations, the adhesive layer covering 130 is configured to cover the adhesive layer 120 prior to usage of the defibrillator hair removal pad 100.

In some implementations, the adhesive layer covering 130 is configured to cover the adhesive layer 120 to preserve the adhesiveness of the adhesive layer 120 prior to usage of the defibrillator hair removal pad 100. For example, in some implementations, the adhesive layer covering 130 is configured to cover the adhesive layer 120 to prevent the adhesive layer 120 from being exposed to dust or other particles that can degrade the adhesiveness of the adhesive layer 120.

In some implementations, the adhesive layer covering 130 is configured to cover the adhesive layer 120 to prevent the adhesive layer 120 from being exposed to any other matter or conditions that can degrade the adhesiveness of the adhesive layer 120. In some implementations, the adhesive layer covering 130 is configured to cover the adhesive layer 120 to prevent the adhesive layer 120 from being exposed to any other matter or conditions that can otherwise deteriorate the adhesive layer 120.

In some implementations, the adhesive layer covering 130 is configured to be removed from the adhesive layer 120. For example, in some implementations, the adhesive layer covering 130 is configured to be removed from the adhesive layer 120 to use the defibrillator hair removal pad 100 to remove body hair with the adhesive layer 120.

In some implementations, the adhesive layer covering 130 is configured to be removed from the adhesive layer 120 by a user of the defibrillator hair removal pad 100 grasping and pulling the adhesive layer covering 130 off of the adhesive layer 120.

In some implementations, the adhesive layer covering 130 is configured to be discarded after the adhesive layer covering 130 is removed from the adhesive layer 120.

In some implementations, the adhesive layer covering 130 may be composed of a durable paper material. For example, in some implementations, the adhesive layer covering 130 may be composed of a durable wax paper material.

In some implementations, the adhesive layer covering 130 may be composed of a durable plastic material.

In some implementations, the adhesive layer covering 130 may be composed of any other suitable material that can accordingly cover and be removably attached to the adhesive layer 120 as described above.

As shown in FIG. 1A, in some implementations, the adhesive layer 120 is securely attached to the main portion 110a of the base 110 on the front side 110c of the base 110. In some implementations, the adhesive layer covering 130 is removably attached to the adhesive layer 120 opposite the attachment of the adhesive layer 120 to the main portion 110a on the front side 110c of the base 110.

In some implementations, the adhesive layer 120, securely attached to the main portion 110a, extends over all or most of the extents of the main portion 110a, which are defined by the sides 110a1, 110f, 110g, 110h as described above.

In some implementations, the adhesive layer 120, securely attached to the main portion 110a, extends over a suitable portion of the extents of the main portion 110a so that the adhesive layer 120 can remove a sufficient surface area, i.e. length, width, and/or shape, of body hair from the skin of a heart attack victim when the defibrillator hair removal pad 100 is used. In some implementations, such sufficient surface area of body hair is larger than the surface area of adhesive electrode pads of an automated external defibrillator (AED) or similar defibrillator device.

In some implementations, the adhesive layer 120 may extend over any other suitable portion of the extents of the main portion 110a of the base 110.

In some implementations, the adhesive layer covering 130, removably attached to the adhesive layer 120, extends over at least all or most of the extents of the adhesive layer 120, which are defined by the sides 120e, 120f, 120g, 120h of the adhesive layer 120 as described above.

In some implementations, the adhesive layer covering 130 extends over and beyond all of the extents of the adhesive layer 120 adjacent to one or more sides 130e, 130f, 130g, 130h of the adhesive layer covering 130. For example, in some implementations, the adhesive layer covering 130 extends beyond the extents of the adhesive layer 120 so that the adhesive layer covering 130 can be more easily grasped and pulled from the adhesive layer 120 for usage of the defibrillator hair removal pad 100 to remove body hair with the adhesive layer 120.

In some implementations, the adhesive layer covering 130 may extend over any other suitable portion of the extents of the adhesive layer 120.

In some implementations, the defibrillator hair removal pad 100 is configured to adhere to and remove body hair from the skin of a heart attack victim's chest. For example, in some implementations, the defibrillator hair removal pad 100 is configured to stick to and pull the body hair from the skin of the heart attack victim's chest.

In some implementations, the defibrillator hair removal pad 100 is configured to remove the body hair to allow the unobstructed and secure sticking of adhesive electrode pads of an automated external defibrillators (AED) or similar defibrillator device to the skin of the heart attack victim's chest.

In some implementations, the defibrillator hair removal pad 100 is configured to allow the unobstructed and secure sticking of the adhesive electrode pads so that the AED can be properly used to administer life-saving electrical impulses to the victim's heart.

In some implementations, the defibrillator hair removal pad 100 is configured to allow the defibrillator hair removal pad 100 to be quickly and easily pulled to remove the body hair from the skin of a heart attack victim's chest.

In some implementations, the defibrillator hair removal pad 100 is configured to remove a surface area, i.e. length, width, and/or shape, of the body hair that is larger than the surface area of the AED adhesive electrode pad. In some implementations, the defibrillator hair removal pad 100 is configured to remove such larger surface area of the body hair so that the entire contact surface of the AED adhesive electrode pads can be fully and easily stuck to the skin of a heart attack victim's chest.

In some implementations, the defibrillator hair removal pad 100 is configured to be sufficiently durable to allow the defibrillator hair removal pad 100 to be quickly and easily pulled to remove the body hair from the skin of a heart attack victim without tearing or otherwise damaging the defibrillator hair removal pad 100. For example, in some implementations, the defibrillator hair removal pad 100, such as the base layer 110, may be rip/tear-resistant or rip/tear-proof.

In some implementations, the defibrillator hair removal pad 100 is configured to provide a sufficient amount of adhesive to quickly, easily, and sufficiently adhere to and remove the body hair from the skin of a heart attack victim.

In some implementations, the defibrillator hair removal pad 100 is configured to be used to remove the body hair from the skin of a heart attack victim without causing a risk of injury or of creating a biological hazard, e.g. in contrast to using a razor. For example, in some implementations, the defibrillator hair removal pad 100 is configured to be used to remove the body hair from the skin of a heart attack victim without causing such risk to the heart attack victim or the AED user, such as a first responder or other concerned person.

Figure 2:
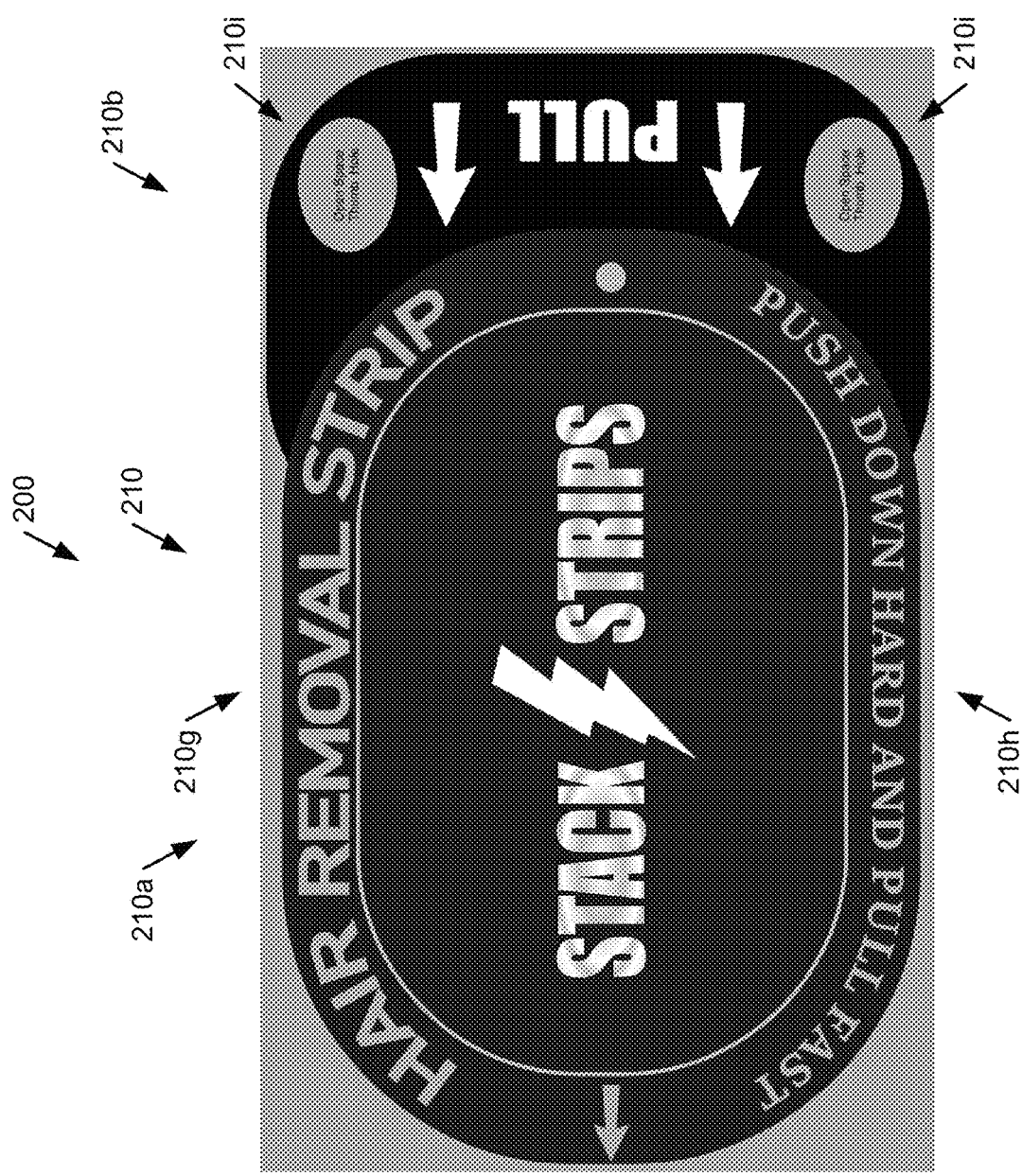
FIG. 2 illustrates another implementation of an example body hair removal pad for defibrillator usage according to the present disclosure.

FIG. 2 illustrates another implementation of an example body hair removal pad for defibrillator usage ("defibrillator hair removal pad") 200 according to the present disclosure.

In some implementations, the defibrillator hair removal pad 200 is similar to the defibrillator hair removal pad 100 described above with respect to FIGS. 1A and 1B. That is, as shown in FIG. 2, in some implementations, the defibrillator hair removal pad 200 comprises, among other similarities, a base 210 that comprises a main portion 210a, a pull tab portion 210b, a top side 210g, and a bottom side 210h. Also, in some implementations, the defibrillator hair removal pad 200 comprises (not shown) an adhesive layer 220 and an adhesive layer covering 230.

Furthermore, in some implementations, the defibrillator hair removal pad 200 is configured to remove body hair from the skin of a heart attack victim to allow the proper attachment of adhesive electrode pads of an automated external defibrillator (AED) or similar defibrillator device to administer life-saving electrical impulses to the victim's heart.

As shown in FIG. 2, in some implementations, the defibrillator hair removal pad 200 may vary in similarity to the defibrillator hair removal pad 100 by one or more components being rectangular or curved rectangular shaped, such as the base 210, the main portion 210a, the adhesive layer 220, and/or the adhesive layer covering 230. However, in some implementations, one or more of such components may have any other suitable shape and/or dimensional proportions.

As shown in FIG. 2, in some implementations, the defibrillator hair removal pad 200 also comprises one or more pull tab openings 210i. In some implementations, the defibrillator hair removal pad 200 comprises two pull tab openings 210i. In some implementations, the defibrillator hair removal pad 200 may comprise more than two pull tab openings 210i. In some implementations, the defibrillator hair removal pad 200 may comprise less than two pull tab openings 210i.

In some implementations, the pull tab openings 210i extend through the pull tab portion 210b of the base 210 of the defibrillator hair removal pad 200.

In some implementations, the pull tab openings 210i are positioned on the pull tab portion 210b adjacent to the top side 210g and the bottom side 210h of the base 210 respectively. In some implementations, the pull tab openings 210i are positioned in any other suitable location on the pull tab portion 210b of the base 210.

In some implementations, the pull tab openings 210i are oval shaped. In some implementations, the pull tab openings 210i may be circular shaped. In some implementations, the pull tab openings 210i may be any other suitable shape.

In some implementations, the pull tab openings 210i are configured to allow a user of the defibrillator hair removal pad 200 to insert one or more of the user's fingers into and/or through the pull tab openings 210i.

In some implementations, the pull tab openings 210i are configured to thereby allow the user of the defibrillator hair removal pad 200 to get a better and/or firmer grip on the defibrillator hair removal pad 200 by the pull tab portion 210b. For example, in some implementations, the pull tab openings 210i are configured to allow the user of the defibrillator hair removal pad 200 to get a better and/or firmer grip to pull the defibrillator hair removal pad 200 by the pull tab portion 210b to remove body hair from the skin of a heart attack victim.

Figure 3:
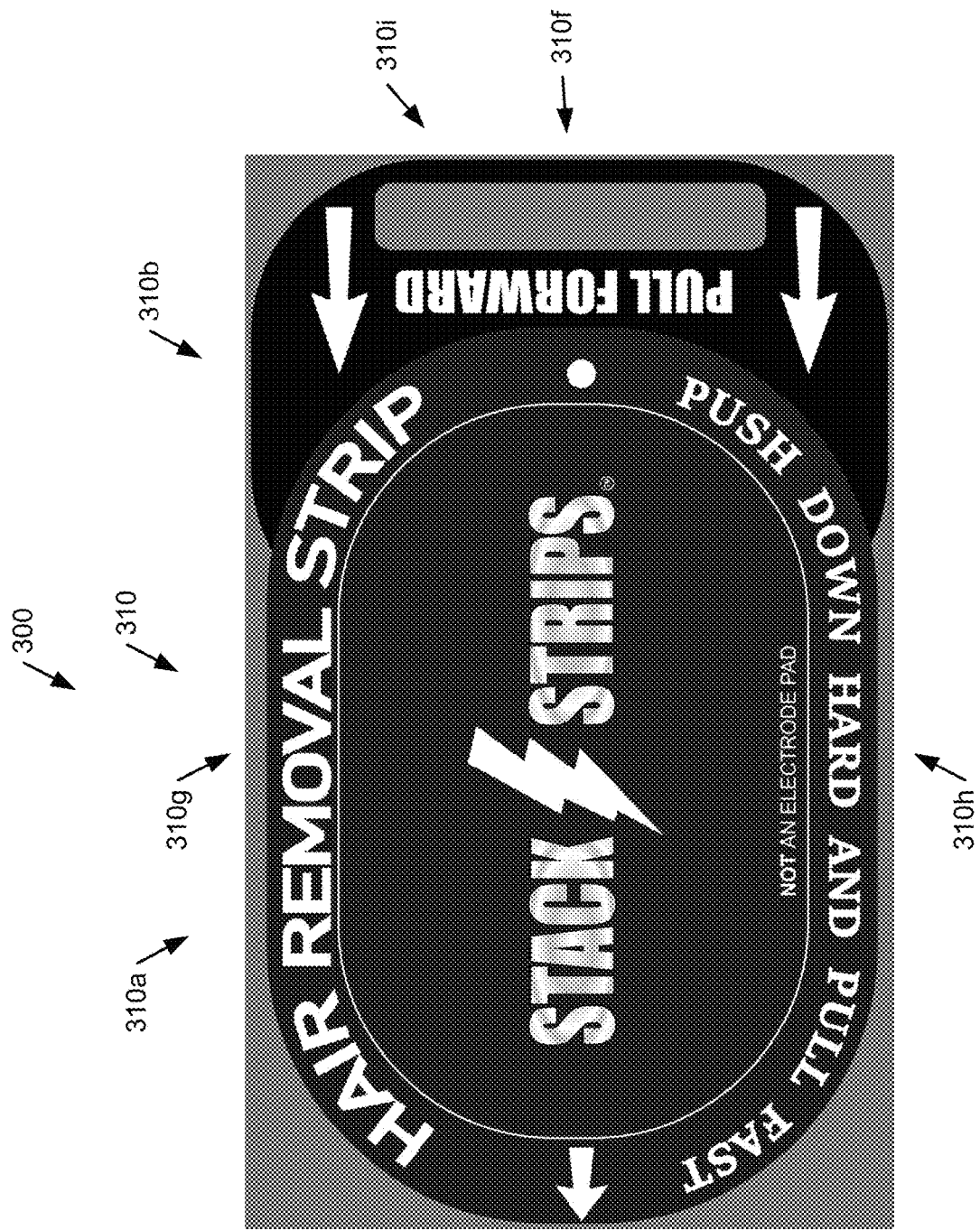
FIG. 3 illustrates another implementation of an example body hair removal pad for defibrillator usage according to the present disclosure.

FIG. 3 illustrates another implementation of an example body hair removal pad for defibrillator usage ("defibrillator hair removal pad") 300 according to the present disclosure.

In some implementations, the defibrillator hair removal pad 300 is similar to the defibrillator hair removal pad 100 described above with respect to FIGS. 1A and 1B. That is, as shown in FIG. 3, in some implementations, the defibrillator hair removal pad 300 comprises, among other similarities, a base 310 that comprises a main portion 310a, a pull tab portion 310b, a right side 310f, a top side 310g, and a bottom side 310h. Also, in some implementations, the defibrillator hair removal pad 300 comprises (not shown) an adhesive layer 320 and an adhesive layer covering 330.

Furthermore, in some implementations, the defibrillator hair removal pad 300 is configured to remove body hair from the skin of a heart attack victim to allow the proper attachment of adhesive electrode pads of an automated external defibrillator (AED) or similar defibrillator device to administer life-saving electrical impulses to the victim's heart.

As shown in FIG. 3, in some implementations, the defibrillator hair removal pad 300 may vary in similarity to the defibrillator hair removal pad 100 by one or more components being rectangular or curved rectangular shaped, such as the base 310, the main portion 310a, the adhesive layer 320, and/or the adhesive layer covering 330. However, in some implementations, one or more of such components may have any other suitable shape and/or dimensional proportions.

As shown in FIG. 3, in some implementations, the defibrillator hair removal pad 300 also comprises a pull tab opening 310i. In some implementations, the defibrillator hair removal pad 300 may comprise more than one pull tab opening 310i.

In some implementations, the pull tab opening 310i extends through the pull tab portion 310b of the base 310 of the defibrillator hair removal pad 300.

In some implementations, the pull tab opening 310i is positioned on the pull tab portion 310b between the top side 310g and the bottom side 310h of the base 310 adjacent to the right side 310f of the base 310. In some implementations, the pull tab opening 310i is positioned in any other suitable location on the pull tab portion 310b.

In some implementations, the pull tab opening 310i is rectangular or curved rectangular shaped. In some implementations, the pull tab opening 310i may be any other suitable shape.

In some implementations, the pull tab opening 310i is configured to allow a user of the defibrillator hair removal pad 300 to insert one or more of the user's fingers into and/or through the pull tab opening 310i.

In some implementations, the pull tab opening 310i is configured to thereby allow the user of the defibrillator hair removal pad 300 to get a better and/or firmer grip on the defibrillator hair removal pad 300 by the pull tab portion 310b. For example, in some implementations, the pull tab opening 310i is configured to allow the user of the defibrillator hair removal pad 300 to get a better and/or firmer grip to pull the defibrillator hair removal pad 300 by the pull tab portion 310b to remove body hair from the skin of a heart attack victim.

Figure 4A:
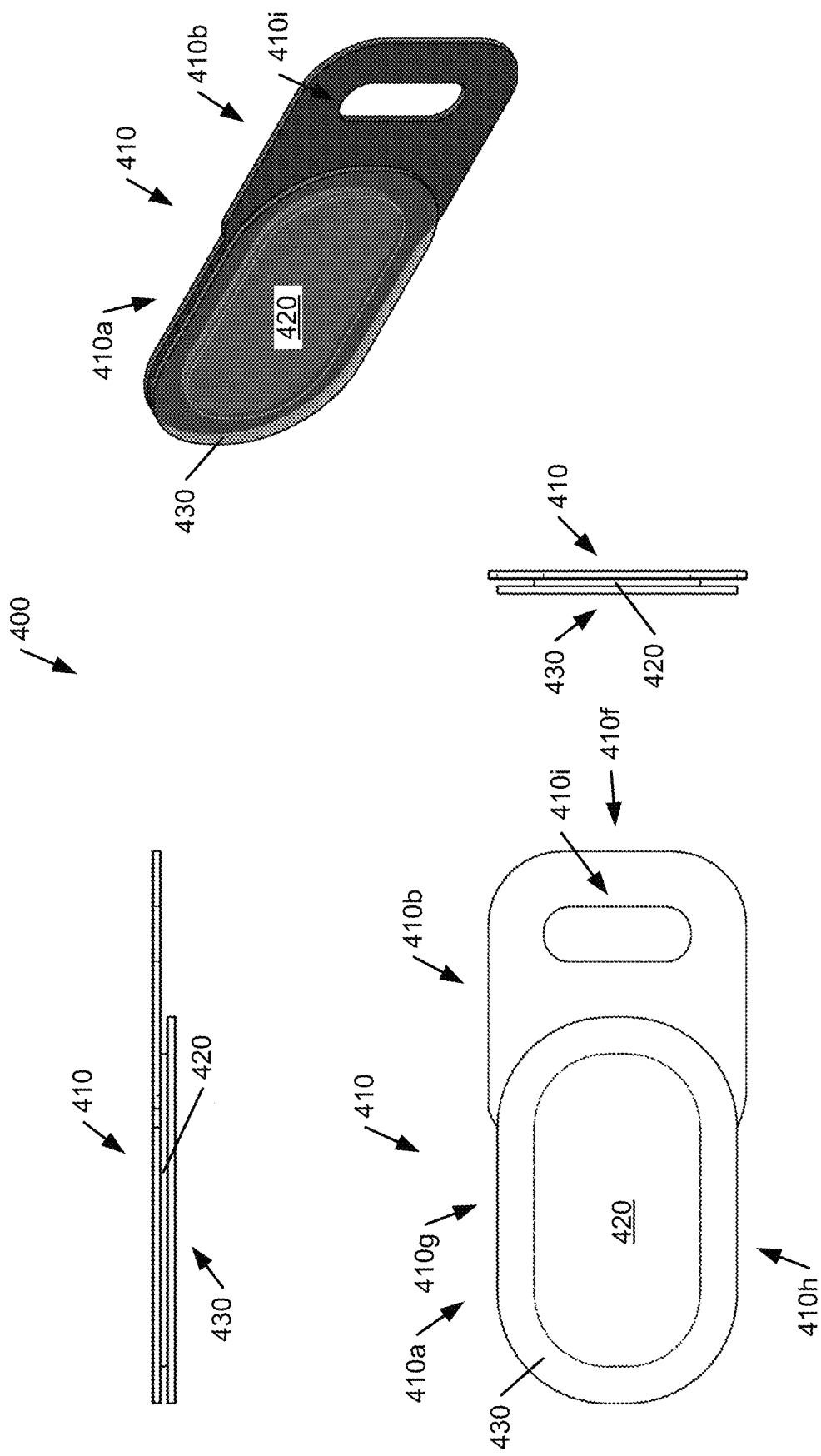
FIGS. 4A and 4B illustrate various views of another implementation of an example body hair removal pad for defibrillator usage according to the present disclosure.
Figure 4B:
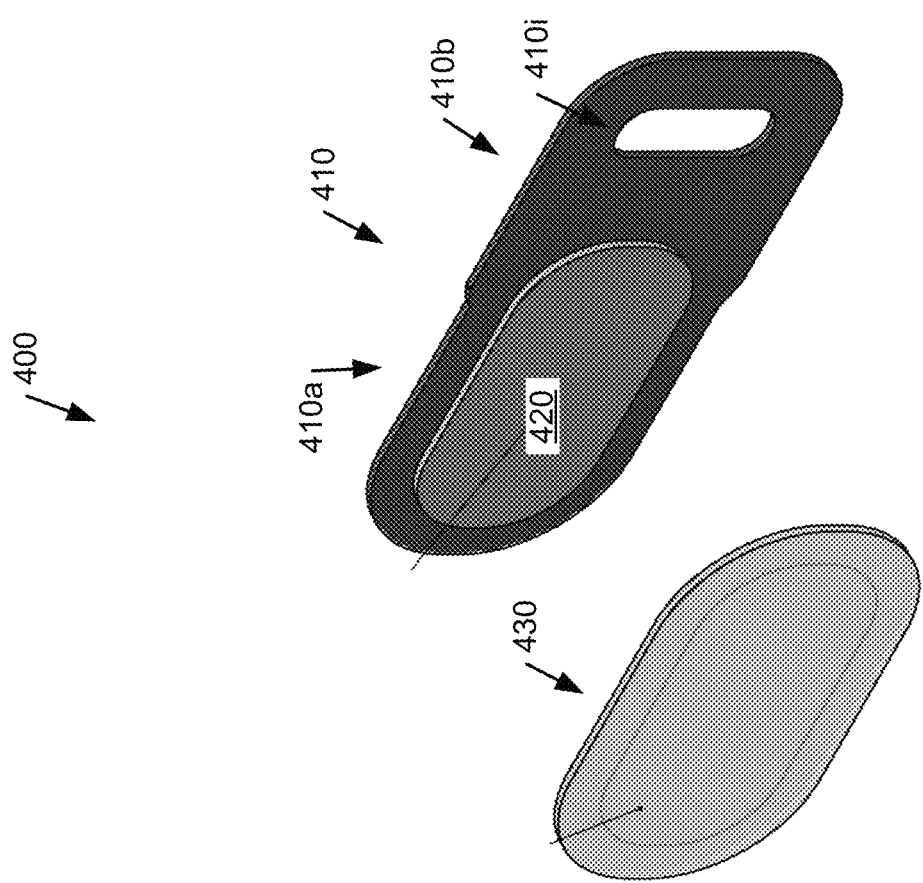

FIGS. 4A and 4B illustrate various views of another implementation of an example body hair removal pad for defibrillator usage ("defibrillator hair removal pad") 400 according to the present disclosure.

In some implementations, the defibrillator hair removal pad 400 is similar to the defibrillator hair removal pad 100 described above with respect to FIGS. 1A and 1B. That is, as shown in FIG. 4A, in some implementations, the defibrillator hair removal pad 400 comprises, among other similarities, a base 410 that comprises a main portion 410a, a pull tab portion 410b, a right side 410f, a top side 410g, and a bottom side 410h.

Also, in some implementations, the defibrillator hair removal pad 400 comprises an adhesive layer 420 and an adhesive layer covering 430. In some implementations, other similarities of the defibrillator hair removal pad 400 to the defibrillator hair removal pad 100 are indicated by like numbered elements shown in FIGS. 4A and 4B.

Furthermore, in some implementations, the defibrillator hair removal pad 400 is configured to remove body hair from the skin of a heart attack victim to allow the proper attachment of adhesive electrode pads of an automated external defibrillator (AED) or similar defibrillator device to administer life-saving electrical impulses to the victim's heart.

In some implementations, the defibrillator hair removal pad 400 is also similar to the defibrillator hair removal pad 300 described above with respect to FIG. 3. That is, as shown in FIG. 4A, in some implementations, the defibrillator hair removal pad 400 comprises, among other similarities, a rectangular or curved rectangular shaped pull tab opening 410i that extends through the pull tab portion 410b of the base 410. Also, in some implementations, one or more components of the defibrillator hair removal pad 400 may be rectangular or curved rectangular shaped, such as the base 410, the main portion 410a, the adhesive layer 420, and/or the adhesive layer covering 430.

Furthermore, in some implementations, the defibrillator hair removal pad 400 is configured to allow a user to insert one or more of the user's fingers into and/or through the pull tab opening 410i to get a better and/or firmer grip on the defibrillator hair removal pad 400 by the pull tab portion 410b.

Figure 5A:
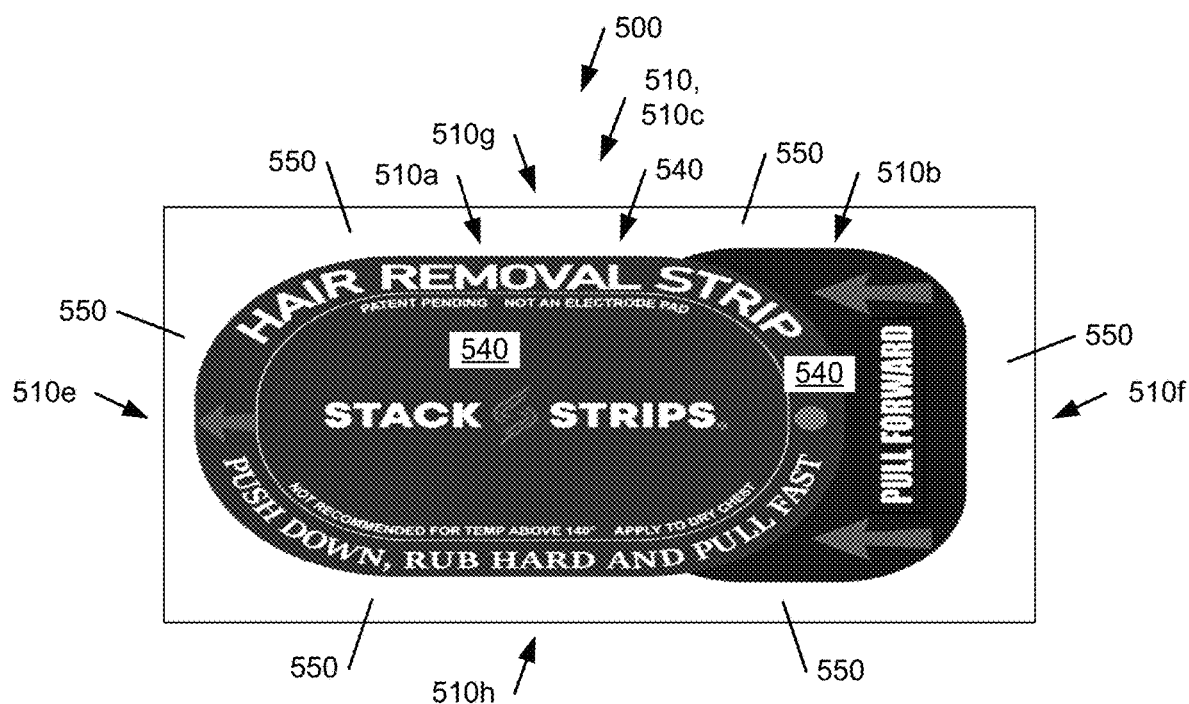
FIGS. 5A-5C illustrate another implementation of an example body hair removal pad for defibrillator usage according to the present disclosure.
Figure 5B:
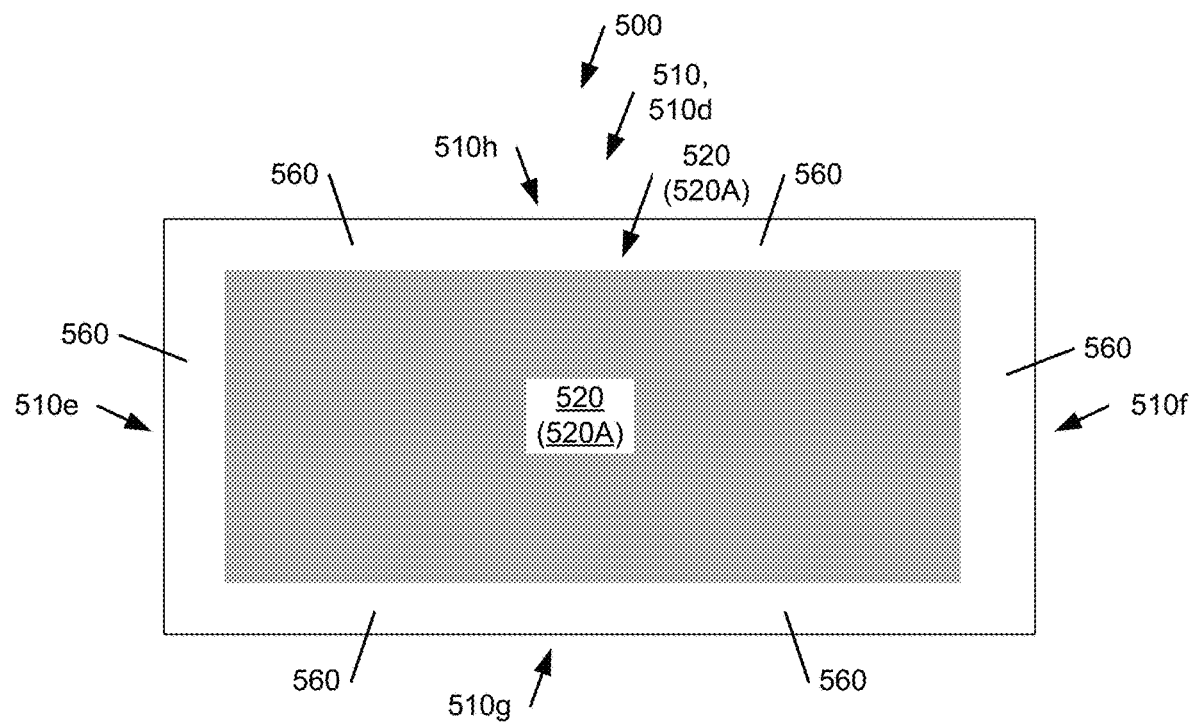
Figure 5C:
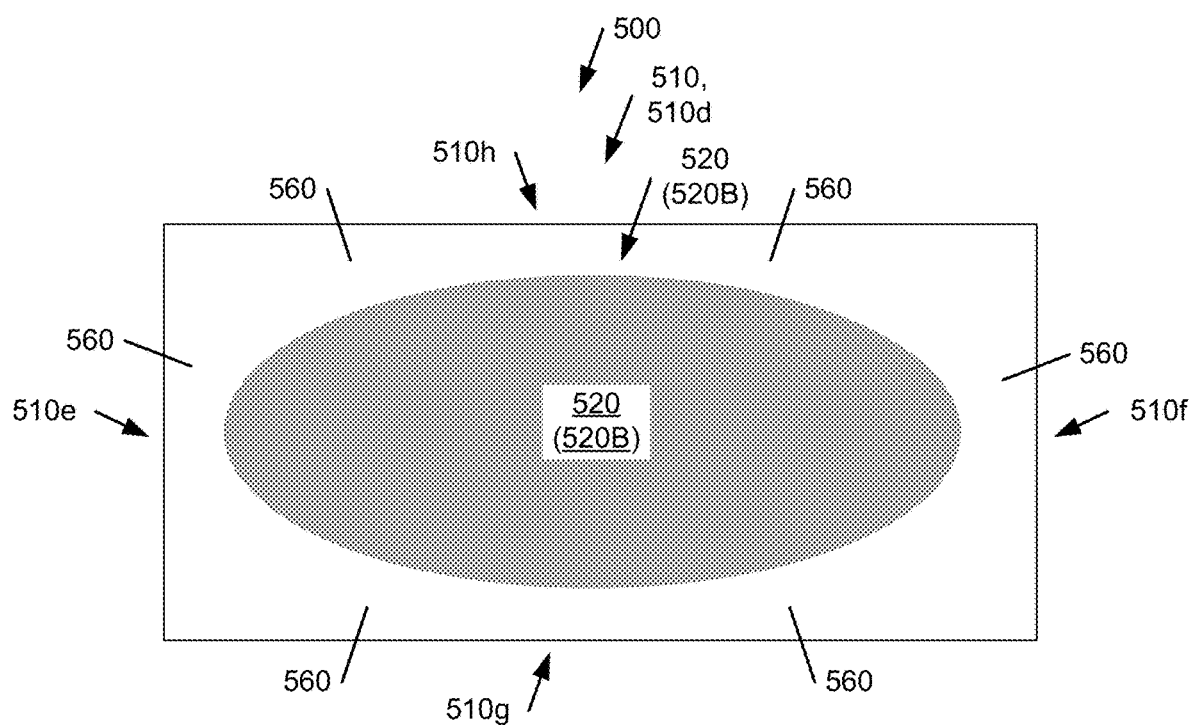

FIGS. 5A-5C illustrate another implementation of an example body hair removal pad for defibrillator usage ("defibrillator hair removal pad") 500 according to the present disclosure.

In some implementations, the defibrillator hair removal pad 500 is similar to the defibrillator hair removal pad 100, 200, 300, 400 described above with respect to FIGS. 1A-1B, 2, 3, and 4A-4B.

For example, as shown in FIG. 5A, in some implementations, the defibrillator hair removal pad 500 comprises a base 510 that comprises a front side/surface 510c, a left side 510e, a right side 510f, a top side 510g, and a bottom side 510h. As shown in FIGS. 5B and 5C, in some implementations, the defibrillator hair removal pad 500 also comprises an adhesive layer 520 and the base 510 also comprises a back side/surface 510d.

In some implementations, the defibrillator hair removal pad 500 also comprises an adhesive layer covering (not shown) that is similar to the above described adhesive layer covering 130, 430.

As shown in FIG. 5A, in some implementations, the defibrillator hair removal pad 500 further comprises a label 540, as described below.

Figure 8:
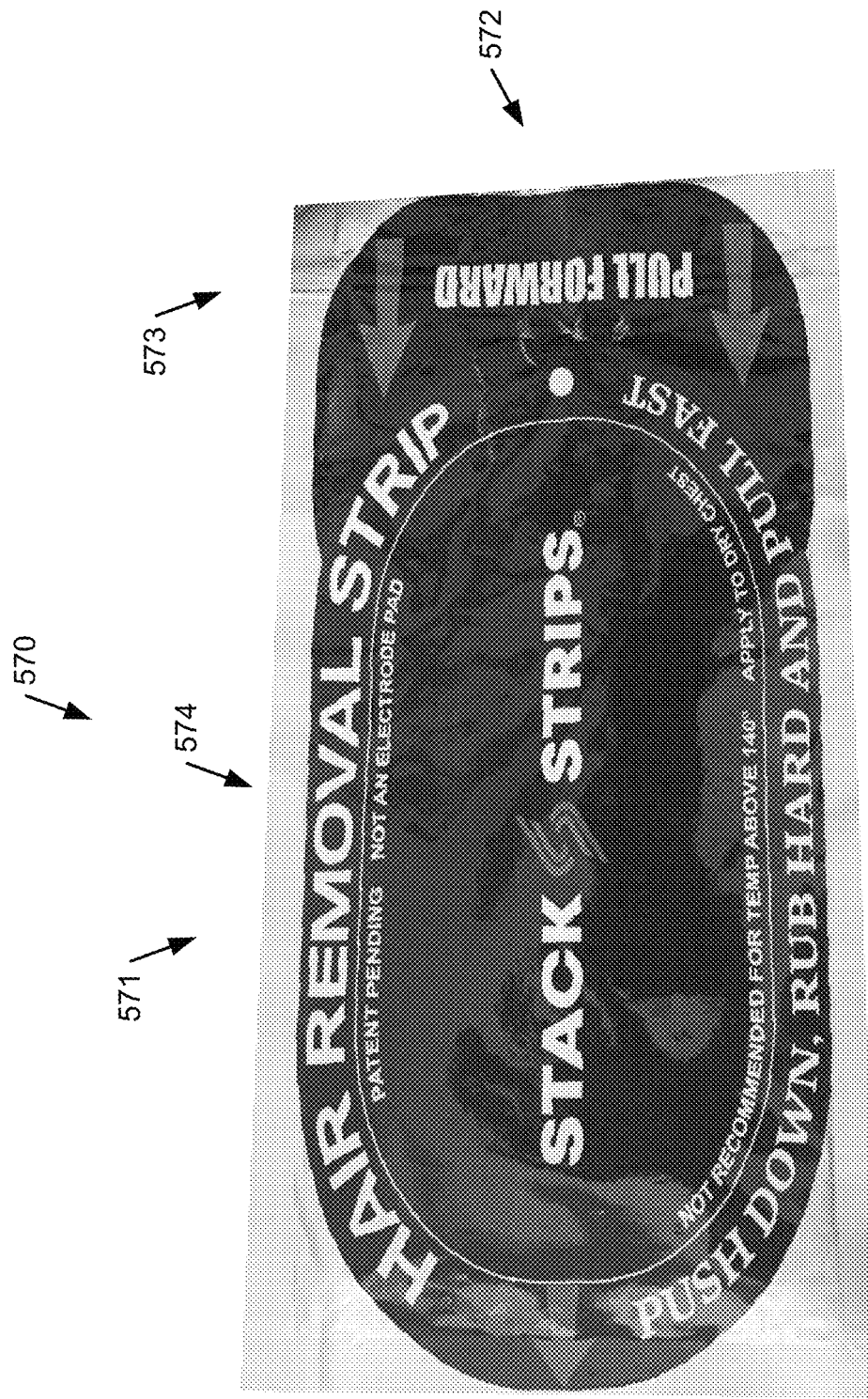
FIG. 8 illustrates a thermal enclosure of the body hair removal pad for defibrillator usage according to the present disclosure.

As shown in FIG. 8, in some implementations, the defibrillator hair removal pad 500 may further comprise a thermal enclosure 570, as described below.

In some implementations, the base 510 may be any suitable shape. For example, in some implementations, the front surface 510c may extend lengthwise and widthwise. In some implementations, the back surface 510d may extend lengthwise and widthwise opposite the front surface 510c.

As shown in FIGS. 5A and 5B, in some implementations, the front and back surfaces 510c, 510d may each extend lengthwise between the left side 510e and the right side 510f of the base 510. In some implementations, the front and back surfaces 510c, 510d may each extend widthwise between the top side 510g and the bottom side 510f of the base 510. In some implementations, the base 510 may thereby be at least generally rectangular prism shaped.

As shown in FIG. 5A, in some implementations, the label 540 is similar to the main portion 210a, 310a and the pull tab portion 210b, 310b of the defibrillator hair removal pad 200, 300 of FIGS. 2 and 3. For example, in some implementations, the label 540 is shaped similar to the combination of the main portion 210a, 310a and the pull tab portion 210b, 310b, such as an at least generally rectangular or curved rectangular shape.

As shown in FIG. 5A, in some implementations, the label 540 may comprise a first portion 510a and a second portion 510b that are similar respectively to the main portion 210a, 310a and the pull tab portion 210b, 310b of the defibrillator hair removal pad 200, 300. For example, in some implementations, the first portion 510a may be at least generally oval shaped or semi-oval shaped. In some implementations, the second portion 510b may extend from the first portion 510a, such as from the right side, and be at least generally rectangular or curved rectangular shape.

In some implementations, the label 540 may be any other suitable shape. For example, in some implementations, the label 540 may generally extend lengthwise and widthwise in any suitable shape similar to the front surface 510c of the base 510 as described above.

In some implementations, the label 540 has a similar appearance to the main portion 210a, 310a and the pull tab portion 210b, 310b of the defibrillator hair removal pad 200, 300. For example, in some implementations, the label 540 comprises similar markings, such as words, symbols, etc., to the main portion 210a, 310a and the pull tab portion 210b, 310b.

As shown in FIG. 5A, in some implementations, the label 540 comprises markings that indicate information related to the defibrillator hair removal pad 500. For example, in some implementations, the label 540 comprises markings that indicate how to use the defibrillator hair removal pad 500, such as how to apply and/or remove the defibrillator hair removal pad 500 to remove body hair from the skin of a heart attack victim, such as described below.

As shown in FIG. 5A, in some implementations, the label 540 comprises markings that are symbols, such as arrows indicating the direction to apply and/or remove the defibrillator hair removal pad 500. In some implementations, the label 540 comprises markings that are words instructing how to use the defibrillator hair removal pad 500.

In some implementations, the label 540 may comprise any other suitable markings or other content related to the defibrillator hair removal pad 500.

As shown in FIG. 5A, in some implementations, the label 540 is positioned on the front surface 510c of the base 510. In some implementations, the label 540 is positioned in between the sides 510e, 510f, 510g, 510h of the base 510. For example, in some implementations, the label 540 may be positioned at least generally centered lengthwise between the left side 510e and the right side 510f of the base 510. In some implementations, the label 540 may be positioned at least generally centered widthwise between the top side 510g and the bottom side 510h of the base 510.

In some implementations, the label 540 may extend lengthwise at least partly to the left side 510e and/or to the right side 510f of the base 510. In some implementations, the label 540 may extend widthwise at least partly to the top side 510g and/or to the bottom side 510h of the base 510. For example, as shown in FIG. 5A, in some implementations, the base 510 may comprise a first border portion 550 between one or more respective sides of the label 540 and of the base 510.

In some implementations, the label 540 is positioned on the base 510 such that the second portion 510b of the label 540 is adjacent to the right side 510f of the base 510. In some implementations, the label 540 may be positioned on the base 510 such that the second portion 510b of the label 540 is adjacent to any other suitable side of the base 510.

In some implementations, the label 540 is positioned on the base 510 such that the adhesive layer 520 is positioned on the back side 510d of the base 510 at least generally opposite the label 540. For example, in some implementations, the label 540 is positioned on the base 510 such that the label 540 provides a reference (e.g., a visual reference) to the location of the adhesive layer 520 when using the defibrillator hair removal pad 500, as described below.

In some implementations, the label 540 may be positioned at any other suitable location of the base 510. In some implementations, the label 540 may be positioned in any other suitable way on the base 510.

In some implementations, the label 540 may be attached to or part of the base 510 in any suitable way. For example, in some implementations, the label 540 may be printed on the base 510. In some implementations, the label 540 may be an integrated part of the base 510.

In some implementations, the label 540 is configured to indicate information related to the defibrillator hair removal pad 500, such as how to use the defibrillator hair removal pad 500. For example, in some implementations, the label 540 is configured to indicate how to apply and/or remove the defibrillator hair removal pad 500 to remove body hair from the skin of a heart attack victim.

In some implementations, the label 540 may be configured to indicate any other suitable information or content related to the defibrillator hair removal pad 500.

In some implementations, the label 540 is configured to provide a reference, e.g. a visual reference, to the location of the adhesive layer 520 when using the defibrillator hair removal pad 500.

In some implementations, the label 540 may be configured to provide any other suitable feature of the defibrillator hair removal pad 500.

In some implementations, the adhesive layer 520 may be any suitable shape. For as example, as shown in FIG. 5B, in some implementations, the adhesive layer 520 (520A) may be at least generally rectangular shaped. As shown in FIG. 5C, in some implementations, the adhesive layer 520 (520B) may be at least generally oval shaped.

In some implementations, the adhesive layer 520 may generally extend lengthwise and widthwise in any suitable shape similar to the back surface 510d of the base 510 as described above.

In some implementations, the adhesive layer 520 may be sized, e.g. in length and width, such that the extents/bounds of the adhesive layer 520 are less than the extents/bounds of the label 540. In some implementations, the adhesive layer 520 may be sized such that the extents of the adhesive layer 520 are the same or similar to the extents of the label 540. In some implementations, the adhesive layer 520 may be sized such that the extents of the adhesive layer 520 are greater than the extents of the label 540.

As shown in FIGS. 5B and 5C, in some implementations, the adhesive layer 520 is positioned on the back surface 510*d* of the base 510. In some implementations, the adhesive layer 520 is positioned in between the sides 510*e*, 510*f*, 510*g*, 510*h* of the base 510. For example, in some implementations, the adhesive layer 520 may be positioned at least generally centered lengthwise between the left side 510*e* and the right side 510*f* of the base 510. In some implementations, the adhesive layer 520 may be positioned at least generally centered widthwise between the top side 510*g* and the bottom side 510*h* of the base 510.

In some implementations, the adhesive layer 520 may extend lengthwise at least partly to the left side 510*e* and/or to the right side 510*f* of the base 510. In some implementations, the adhesive layer 520 may extend widthwise at least partly to the top side 510*g* and/or to the bottom side 510*h* of the base 510. For example, as shown in FIGS. 5B and 5C, in some implementations, the base 510 may comprise a second border portion 560 between one or more respective sides of the adhesive layer 520 and of the base 510.

In some implementations, the adhesive layer 520 is positioned on the back side 510*d* of the base 510 at least generally opposite the label 540 positioned on the front side 510*c* of the base 510. For example, in some implementations, the adhesive layer 520 is positioned on the base 510 such that the label 540 provides a reference (e.g., a visual reference) to the location of the adhesive layer 520 when using the defibrillator hair removal pad 500, as described below.

In some implementations, the adhesive layer 520 may be positioned at any other suitable location of the base 510. In some implementations, the adhesive layer 520 may be positioned in any other suitable way on the base 510.

In some implementations, the adhesive layer 520 is configured to be positioned by the base 510 on the skin of a heart attack victim based on the position of the label 540, which provides a reference (e.g., a visual reference), to the location of the adhesive layer 520 when using the defibrillator hair removal pad 500.

In some implementations, the adhesive layer 520 is configured to be removed (e.g., pulled away) from the skin of a heart attack victim by a user of the defibrillator hair removal pad 500 grasping and pulling the base 510 at the first border portion 550 and the second border portion 560, such as shown in FIGS. 6D-6E and 7D-7E. For example, in some implementations, the adhesive layer 520 is configured to be removed from the victim's skin by the user grasping and pulling the base 510 at the border portions 550, 560 adjacent to the right side 510*f* of the base 510.

In some implementations, the adhesive layer 520 may be configured to be removed from the skin of a heart attack victim by a user of the defibrillator hair removal pad 500 grasping and pulling the base 510 at any other suitable location.

In addition to the above described examples for the base 110, 210, 310, 410, in some implementations, the base 510 (as well as the base 110, 210, 310, 410) may be 7.5 inches in length. In some implementations, the base 510 may be greater than 7.5 inches in length. In some implementations, the base 510 may be less than 7.5 inches in length.

In some implementations, the base 510 (as well as the base 110, 210, 310, 410) may be 3.5 inches in width. In some implementations, the base 510 may be greater than 3.5 inches in width. In some implementations, the base 510 may be less than 3.5 inches in width.

In addition to the above described examples for the adhesive layer 120, 220, 320, 420, in some implementations, the adhesive layer 520 (as well as the adhesive layer 120, 220, 320, 420) may be 6 inches in length. In some implementations, the adhesive layer 520 may be greater than 6 inches in length. In some implementations, the adhesive layer 520 may be less than 6 inches in length.

In some implementations, the adhesive layer 520 (as well as the adhesive layer 120, 220, 320, 420) may be 2.75 inches in width. In some implementations, the adhesive layer 520 may be greater than 2.75 inches in width. In some implementations, the adhesive layer 520 may be less than 2.75 inches in width.

In addition to the above described examples for the adhesive layer 120, 220, 320, 420, in some implementations, the adhesive layer 520 (as well as the adhesive layer 120, 220, 320, 420) may be composed of a depilatory wax. In some implementations, the depilatory wax may comprise one or more substances.

In some implementations, the depilatory wax may comprise titanium dioxide. In some implementations, the depilatory wax may comprise a perfume.

In some implementations, the depilatory wax may comprise one or more resin acids. In some implementations, the depilatory wax may comprise one or more rosin acids. In some implementations, the depilatory wax may comprise one or more esters with glycerol. In some implementations, such resin acids, rosin acids, and/or esters with glycerol may comprise glyceryl rosinate.

In some implementations, the depilatory wax may comprise a white mineral oil, such as petroleum. In some implementations, the depilatory wax may comprise one or more hydrocarbon waxes, such as pertoleum. In some implementations, the depilatory wax may comprise hydrotreated microcyst. In some implementations, the depilatory wax may comprise one or more formulations of tetrachlorobenzoic acid.

As noted above and shown in FIG. 8, in some implementations, the defibrillator hair removal pad 500 (as well as the defibrillator hair removal pad 100, 200, 300, 400) may further comprise a thermal enclosure 570. In some implementations, the thermal enclosure 570 may be a thermal bag or similar enclosure.

In some implementations, the thermal enclosure 570 may comprise an enclosing portion 571, an opening 572, and a closure 573. In some implementations, the thermal enclosure 570 may further comprise a label 574 on one or more surfaces.

In some implementations, the enclosing portion 571 may comprise the enclosing portion of a bag or similar enclosure. In some implementations, the enclosing portion 571 may comprise the enclosing portion of any other suitable enclosure.

In some implementations, the opening 572 may comprise any suitable opening that allows one or more of the defibrillator hair removal pad 500 to be inserted and removed from the thermal enclosure 570.

In some implementations, the closure 573 may comprise a ziplock closure. For example, in some implementations, the closure 573 may comprise a resealable two part strip closure along the opening. In some implementations, the closure 573 may comprise a resealable interlocking groove and ridge closure along the opening.

In some implementations, the closure 573 may comprise any other suitable closure that allows the opening to be openable and closable, such as resealable.

As noted above, in some implementations, the thermal enclosure 570 may further comprise a label 574. As shown in FIG. 8, in some implementations, the label 574 may be the same or similar to the label 540 described above. In some implementations, the label may comprise any other suitable features.

In some implementations, the thermal enclosure 570 may be any suitable shape. For example, as shown in FIG. 8, in some implementations, the enclosing portion 571 may extend lengthwise and widthwise such that the thermal enclosure 570 is at least generally rectangular prism shaped.

In some implementations, the thermal enclosure 570 is configured to hold or otherwise enclose one or more the defibrillator hair removal pad 500. For example, in some implementations, the thermal enclosure 570 may be configured to enclose one defibrillator hair removal pad 500.

In some implementations, the thermal enclosure 570 may be configured to enclose two defibrillator hair removal pads 500. In some implementations, the thermal enclosure 570 may be configured to enclose more than two defibrillator hair removal pads 500.

In some implementations, the thermal enclosure 570 is configured to thermally insulate one or more the defibrillator hair removal pad 500 when enclosed in the thermal enclosure. For example, in some implementations, the thermal enclosure 570 may be a thermally insulated bag or similar enclosure.

In some implementations, the thermal enclosure 570 may be configured to thermally insulate the defibrillator hair removal pad 500 from heat, such as to prevent the adhesive layer 520 from melting or otherwise being undesirably affected by heat.

In some implementations, the thermal enclosure 570 may be configured to thermally insulate the defibrillator hair removal pad 500 from cold, such as to prevent the adhesive layer 520 from freezing or otherwise being undesirably affected by cold.

In some implementations, the thermal enclosure 570 may be configured to thermally insulate the defibrillator hair removal pad 500 in any other suitable way. In some implementations, the thermal enclosure 570 may be configured to provide any other suitable feature with respect to the defibrillator hair removal pad 500.

In some implementations, the thermal enclosure 570 may be composed of a foil material. In some implementations, the thermal enclosure 570 may be composed of a coated foil material.

In some implementations, the thermal enclosure 570 may be composed of a coated foil material having an external and/or internal film. For example, in some implementations, the thermal enclosure 570 may comprise a coated foil polybag packaging with an external (and/or internal) polyethylene (PE) film.

In some implementations, the thermal enclosure 570 may be composed of any other suitable material having any other suitable configuration.

Although the defibrillator hair removal pad 100, 200, 300, 400, 500 is described herein with respect to removing body hair from the chest of a heart attack victim, in some implementations, the defibrillator hair removal pad 100, 200, 300, 400, 500 may be configured to remove body hair from any other suitable location of a heart attack victim's body in accordance with the present disclosure.

In some implementations, the defibrillator hair removal pad 100, 200, 300, 400, 500 comprises any suitable dimensions, such as the example dimensions described above.

In some implementations, the defibrillator hair removal pad 100, 200, 300, 400, 500 is composed of any suitable materials, such as the example materials described above.

In some implementations, the defibrillator hair removal pad 100, 200, 300, 400, 500 can have any suitable appearance, such as the example appearances shown in FIGS. 2, 3, and 5A.

In some implementations, an example method of using the defibrillator hair removal pad 100, 200, 300, 400 comprises removing the adhesive layer covering 130, 230, 330, 430 from the adhesive layer 120, 220, 320, 420 of the defibrillator hair removal pad 100, 200, 300, 400.

In some implementations, removing the adhesive layer covering 130, 230, 330, 430 from the adhesive layer 120, 220, 320, 420 comprises grasping and pulling the adhesive layer covering 130, 230, 330, 430 off of the adhesive layer 120, 220, 320, 420.

In some implementations, the adhesive layer covering 130, 230, 330, 430 is removed to expose the adhesive layer 120, 220, 320, 420 for positioning on body hair on the skin of a heart attack victim.

In some implementations, an example method of using the defibrillator hair removal pad 100, 200, 300, 400, 500 comprises positioning the adhesive layer 120, 220, 320, 420, 520 of the defibrillator hair removal pad 100, 200, 300, 400, 500 on body hair on the skin of a heart attack victim. For example, as shown in FIGS. 6A and 7A, in some implementations, the defibrillator hair removal pad 500 is positioned such that the adhesive layer 520 is positioned on body hair on the skin of a heart attack victim.

Figure 6C:
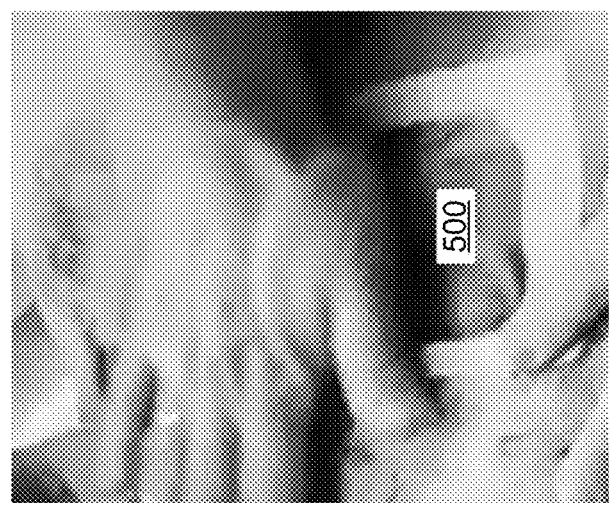
FIGS. 6A-6E illustrate an example use of the body hair removal pad for defibrillator usage according to the present disclosure.
Figure 6B:
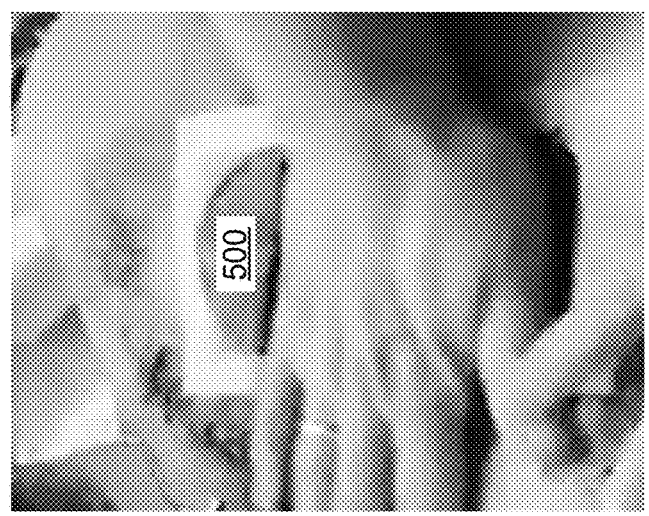
Figure 6A:
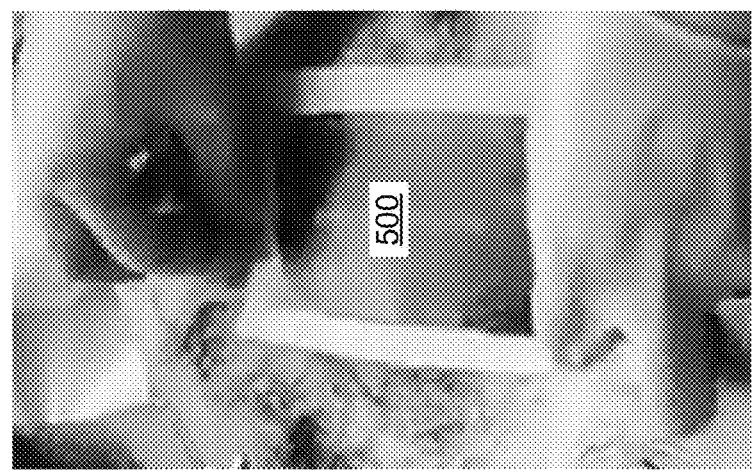
Figure 6E:
Figure 6D:
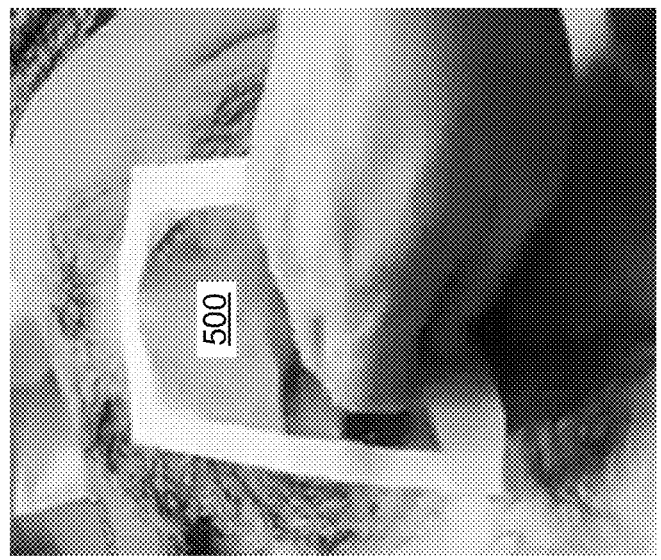
Figure 7A:
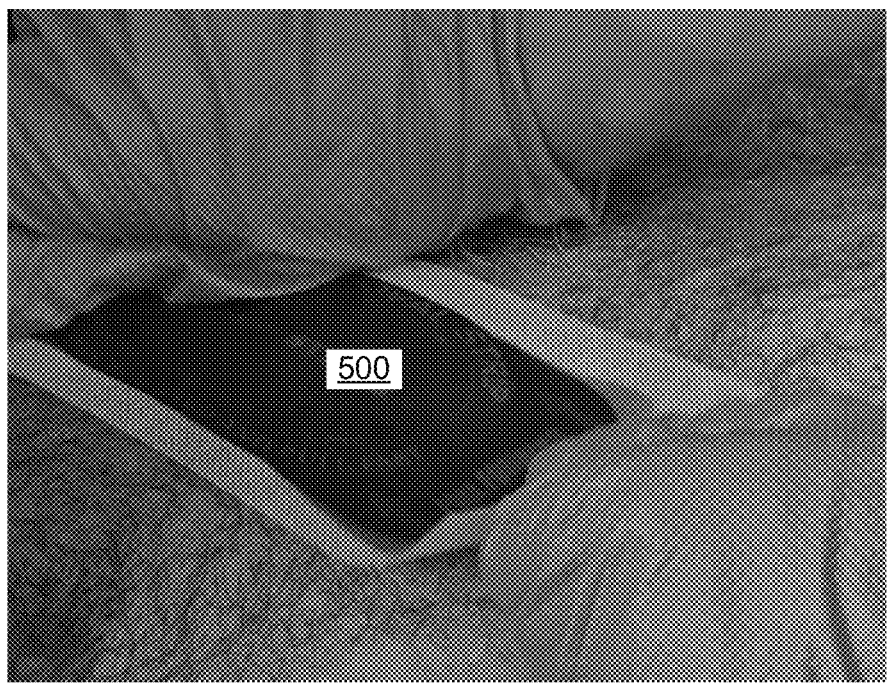
FIGS. 7A-7E illustrate another example use of the body hair removal pad for defibrillator usage according to the present disclosure.
Figure 7B:
Figure 7C:
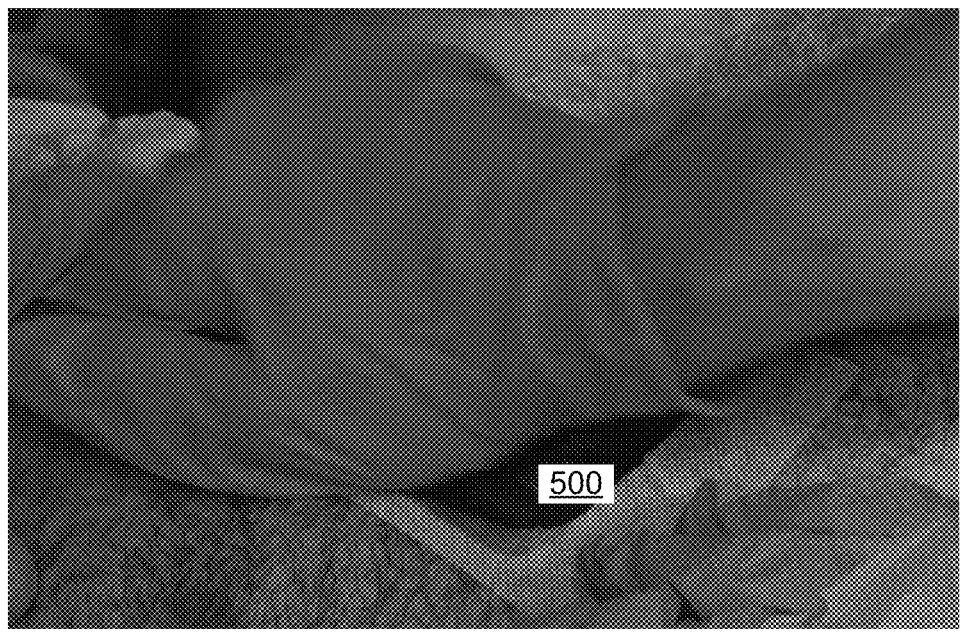
Figure 7D:
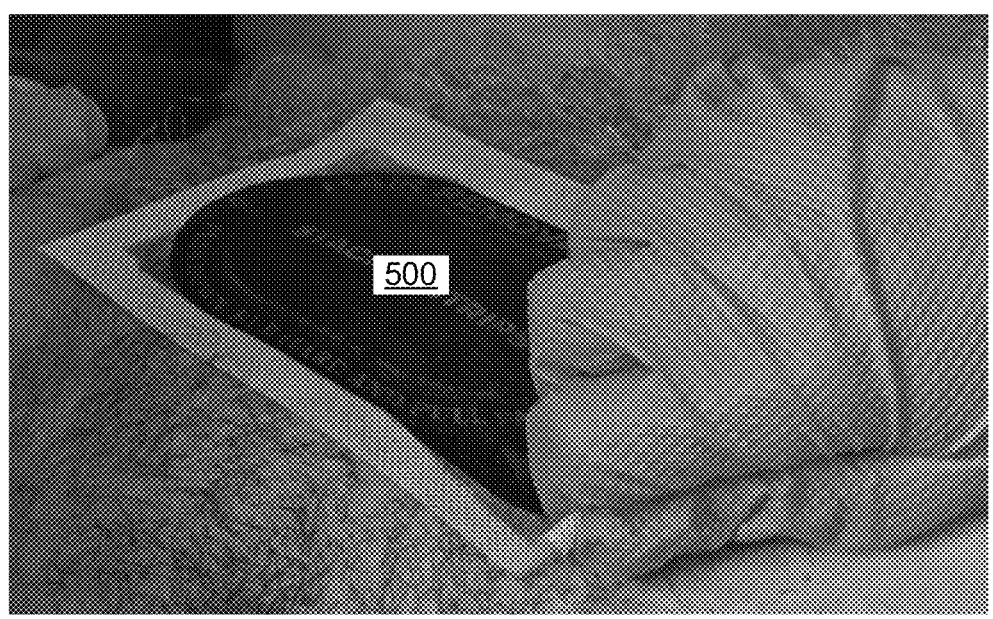
Figure 7E:
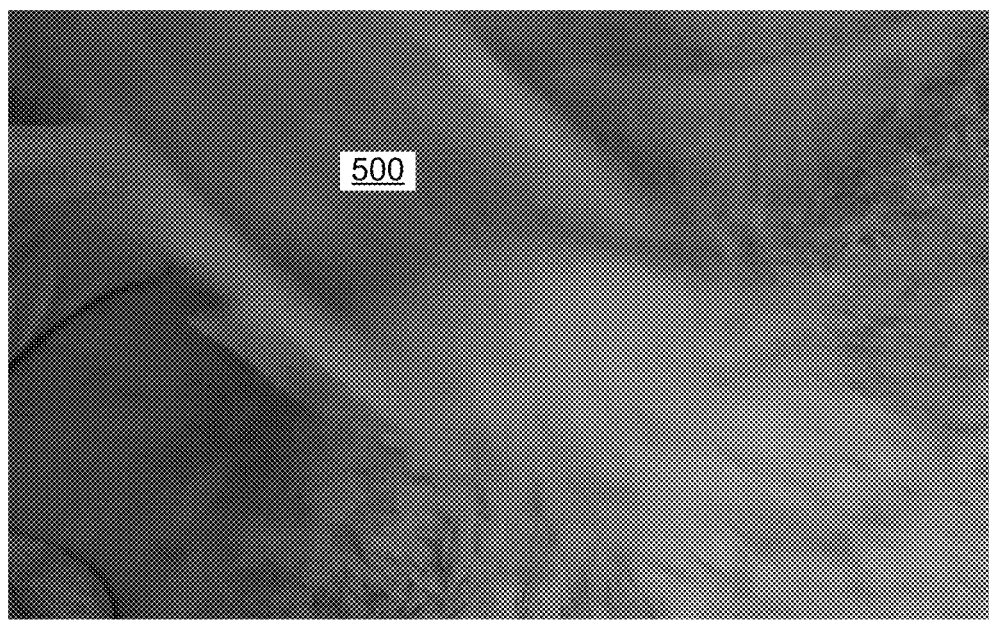

In some implementations, the adhesive layer 120, 220, 320, 420, 520 is positioned by the base 110, 210, 310, 410, 510 of the defibrillator hair removal pad 100, 200, 300, 400, 500, such as shown in FIGS. 6A and 7A.

In some implementations, the adhesive layer 120, 220, 320, 420, 520 is positioned at one of the intended attachment locations of the adhesive electrode pads of an automated external defibrillator (AED) or similar defibrillator device to the skin of the heart attack victim. For example, in some implementations, the adhesive layer 120, 220, 320, 420, 520 is positioned on body hair at such location on the skin of the heart attack victim's chest, such as shown in FIGS. 6A and 7A.

In some implementations, positioning the adhesive layer 520 on body hair on the skin of a heart attack victim comprises positioning the adhesive layer 520, which is facing toward the victim and away from the user, based on the position of the label 540, which is facing toward the user and provides a reference (e.g., a visual reference) to the location of the adhesive layer 520.

In some implementations, positioning the adhesive layer 520 on body hair on the skin of a heart attack victim comprises positioning the adhesive layer 520 by holding the base 510 at the border portions 550, 560 adjacent to one or more sides 510e, 510f, 510g, 510h of the base 510.

In some implementations, positioning the adhesive layer 120, 220, 320, 420, 520 on body hair on the skin of a heart attack victim comprises pressing the adhesive layer 120, 220, 320, 420, 520 onto the body hair on the skin of a heart attack victim, such as shown in FIGS. 6B-6C and 7B-7C. In some implementations, the adhesive layer 120, 220, 320, 420, 520 is pressed onto the body hair on the skin of a heart attack victim by the base 110, 210, 310, 410, 510 of the defibrillator hair removal pad 100, 200, 300, 400, 500, such as shown in FIGS. 6B-6C and 7B-7C.

In some implementations, the adhesive layer 120, 220, 320, 420, 520 is positioned on the skin of a heart attack victim for removing the body hair from the skin, such as from the skin of the heart attack victim's chest.

In some implementations, the method comprises pulling the adhesive layer 120, 220, 320, 420, 520 from the skin of a heart attack victim with the adhesive layer 120, 220, 320, 420, 520 stuck to the body hair on the skin of the heart attack victim, such as shown in FIGS. 6D-6E and 7D-7E.

In some implementations, pulling the adhesive layer 120, 220, 320, 420 from the skin of a heart attack victim comprises pulling the pull tab portion 110b, 210b, 310b, 410b of the base 110, 210, 310, 410 of the defibrillator hair removal pad 100, 200, 300, 400. In some implementations, the adhesive layer 120, 220, 320, 420 is thereby pulled from the skin of the heart attack victim by the main portion 110a, 210a, 310a, 410a of the base 110, 210, 310, 410 of the defibrillator hair removal pad 100, 200, 300, 400.

As shown in FIGS. 6D-6E and 7D-7E, in some implementations, pulling the adhesive layer 520 from the skin of a heart attack victim comprises grasping and pulling the base 510 at the border portions 550, 560, such as adjacent to the right side 510f of the base 510.

In some implementations, the adhesive layer 120, 220, 320, 420, 520 is pulled from the skin of the heart attack victim to remove the body hair from the skin of the heart attack victim, such as from one of the intended attachment locations of the AED adhesive electrode pads to the skin of the heart attack victim as described above.

In some implementations, the defibrillator hair removal pad 100, 200, 300, 400, 500 may be discarded after the defibrillator hair removal pad 100, 200, 300, 400, 500 is used to remove the body hair from the skin of the heart attack victim.

In some implementations, the above described method of using the defibrillator hair removal pad 100, 200, 300, 400, 500 comprises using the defibrillator hair removal pad 100, 200, 300, 400, 500 based on the markings, such as the symbols, words, etc. on the components 210a, 210b, 310a, 310b, 540, that indicate how to use the defibrillator hair removal pad 100, 200, 300, 400, 500.

For example, in some implementations, the defibrillator hair removal pad 100, 200, 300, 400, 500 is positioned and/or pulled as described above based on the symbols, such as the arrows, and/or the words, such as the directions/instructions, marked on the defibrillator hair removal pad 100, 200, 300, 400, 500, such as shown in FIGS. 2, 3, and 5A.

In some implementations, an example method of using the defibrillator hair removal pad 100, 200, 300, 400, 500 may comprise enclosing the defibrillator hair removal pad 100, 200, 300, 400, 500 in a thermal enclosure, such as the thermal enclosure 570. In some implementations, the method may comprise removing the defibrillator hair removal pad 100, 200, 300, 400, 500 from the thermal enclosure.

The figures, including photographs and drawings, comprised herewith may represent one or more implementations of the body hair removal pad for defibrillator usage.

Details shown in the figures, such as dimensions, descriptions, etc., are exemplary, and there may be implementations of other suitable details according to the present disclosure.

Reference throughout this specification to "an embodiment" or "implementation" or words of similar import means that a particular described feature, structure, or characteristic is comprised in at least one embodiment of the present invention. Thus, the phrase "in some implementations" or a phrase of similar import in various places throughout this specification does not necessarily refer to the same embodiment.

Many modifications and other embodiments of the inventions set forth herein will come to mind to one skilled in the art to which these inventions pertain having the benefit of the teachings presented in the foregoing descriptions and the associated drawings.

The described features, structures, or characteristics may be combined in any suitable manner in one or more embodiments. In the above description, numerous specific details are provided for a thorough understanding of embodiments of the invention. One skilled in the relevant art will recognize, however, that embodiments of the invention can be practiced without one or more of the specific details, or with other methods, components, materials, etc. In other instances, well-known structures, materials, or operations may not be shown or described in detail.

While operations may be depicted in the drawings in a particular order, this should not be understood as requiring that such operations be performed in the particular order shown or in sequential order, or that all illustrated operations be performed, to achieve desirable results.

The invention claimed is:

1. A method of using a defibrillator hair removal pad comprising a base layer, an adhesive layer, and an indicator, wherein the base layer comprises a piece of material, the base layer having a perimeter comprising outermost edges completely around the base layer wherein the base layer comprising a first surface extending length-wise and width-wise; and a second surface, opposite the first surface, extending length-wise and width-wise; wherein the adhesive layer is positioned on the second surface of the base layer and comprises a substance configured to adhere to body hair on the skin of a subject such that the body hair can be pulled and removed from the skin by the adhesive layer; and wherein the indicator is positioned on the first surface of the base layer and is configured to indicate from the first surface the position of the adhesive layer on the second surface, the method comprising: positioning the adhesive layer on the body hair on the skin of the subject using the indicator from the first surface of the base layer to determine the position of the adhesive layer on the second surface of the base layer, wherein the adhesive layer does not extend to the outermost edges of the base layer for the entire length of each of the outermost edges and the adhesive layer is positioned such that the adhesive layer is adhered to the body hair and the second surface of the base layer adjacent to the outermost edges of the base layer are not adhered to the subject because of the absence of the substance of the adhesive layer on the second surface of the base layer adjacent to the outermost edges of the base layer for the entire length of each of the outermost edges; pulling and removing the body hair from the skin by pulling the adhesive layer away from the skin; and positioning an adhesive electrode pad of an automated external defibrillator (AED) on the skin where the body hair was removed.

2. The method of claim 1, wherein the base layer comprises at least one opening through the base layer adjacent to an outermost edge of the outermost edges of the base layer, the method further comprising inserting one or more fingers through the at least one opening prior to pulling the adhesive layer away from the skin.

3. The method of claim 1 wherein the indicator is further configured to indicate a direction to pull the base layer to thereby pull the adhesive layer away from the skin of the subject, the method comprising:
  positioning the adhesive layer on the body hair on the skin of the subject using the indicator from the first surface of the base layer to determine the position of the adhesive layer on the second surface of the base layer, wherein the adhesive layer is positioned such that the adhesive layer is adhered to the body hair; and pulling and removing the body hair from the skin by pulling the adhesive layer away from the skin, wherein pulling the adhesive layer comprises pulling the base layer in the direction indicated by the indicator.

4. The method of claim 1, further comprising enclosing the defibrillator hair removal pad in a thermal bag configured to enclose the defibrillator hair removal pad.

5. A method of using a defibrillator hair removal pad, wherein the defibrillator hair removal pad, comprising:
  a base layer, an adhesive layer, and an indicator, wherein:
    the base layer comprises a non-woven piece of material, the base layer comprising:
      a first surface extending length-wise and width-wise; and
      a second surface, opposite the first surface, extending length-wise and width-wise;
    the adhesive layer is positioned on the second surface of the base layer, wherein:
      the adhesive layer comprises a substance configured to adhere to body hair on the skin of a subject such that the body hair can be pulled and removed from the skin by the adhesive layer, wherein the substance comprises a depilatory wax;
      the adhesive layer extends partly lengthwise respective to the length of the second surface of the base layer such that the base layer comprises at least a first exposed portion of the second surface between an edge of the adhesive layer and an adjacent edge of the second surface, wherein:
        the first exposed portion is configured to be contacted while the adhesive layer is adhered to the body hair on the skin of the subject such that the base layer can be held and pulled to thereby pull the adhesive layer away from the skin of the subject; and
      the adhesive layer is sized and shaped such that adhesive layer can pull and remove a portion of the body hair from the skin of the subject that is larger than an adhesive electrode pad of an automated external defibrillator (AED);
    the indicator is positioned on the first surface of the base layer, wherein:
      the indicator comprises a first marking configured to indicate from the first surface the position of the adhesive layer on the second surface; and
      the indicator comprises a second marking configured to indicate how to use the defibrillator hair removal pad,
    wherein the base layer has a perimeter comprising outermost edges completely around the base layer and wherein the adhesive layer extends partly widthwise respective to the width of the second surface of the base layer such that the base layer comprises a second exposed portion of the second surface between each edge of the adhesive layer and an adjacent edge of the second surface such that there is a continuous exposed surface completely around the perimeter of the second surface, the method comprising:
  positioning the adhesive layer on the body hair on the skin of the subject, wherein:
    the adhesive layer is positioned using the first marking of the indicator on the first surface of the base layer to determine the position of the adhesive layer on the second surface of the base layer; and the adhesive layer does not extend to the outermost edges of the base layer for the entire length of the outermost edges and the adhesive layer is positioned such that the adhesive layer is adhered to the body hair by applying contact upon the first surface of the base layer, and the second surface of the base layer adjacent to the outermost edges of the base layer are not adhered to the subject because of the absence of the substance of the adhesive layer on the second surface of the base layer adjacent to the outermost edges of the base layer for the entire length of the outermost edges; and
  pulling and removing the body hair from the skin by pulling the adhesive layer away from the skin, wherein:
    pulling the adhesive layer comprises contacting the first exposed portion of the second surface of the base layer and thereby holding and pulling the base layer to thereby pull the adhesive layer away from the skin; and
    pulling the adhesive layer further comprises pulling the adhesive layer in a direction indicated by the second marking of the indicator.

6. The method of claim 5, wherein the base layer comprises at least one opening through the base layer adjacent to an outermost edge of the outermost edges of the base layer, the method further comprising inserting one or more fingers through the at least one opening prior to pulling the base layer.

7. A method of using a defibrillator hair removal pad, wherein the defibrillator hair removal pad, comprising:
  a base layer, an adhesive layer, and an indicator, wherein:
    the base layer comprises a non-woven piece of material, the base layer comprising:
      a first surface extending length-wise and width-wise; and
      a second surface, opposite the first surface, extending length-wise and width-wise;
    the adhesive layer is positioned on the second surface of the base layer, wherein:
      the adhesive layer comprises a substance configured to adhere to body hair on the skin of a subject such that the body hair can be pulled and removed from the skin by the adhesive layer, wherein the substance comprises a depilatory wax;
      the adhesive layer extends partly lengthwise respective to the length of the second surface of the base layer such that the base layer comprises at least a first exposed portion of the second surface between an edge of the adhesive layer and an adjacent edge of the second surface, wherein:
        the first exposed portion is configured to be contacted while the adhesive layer is adhered to the body hair on the skin of the subject such that the base layer can be held and pulled to thereby pull the adhesive layer away from the skin of the subject; and
      the adhesive layer is sized and shaped such that adhesive layer can pull and remove a portion of the body hair from the skin of the subject that is larger than an adhesive electrode pad of an automated external defibrillator (AED);
    the indicator is positioned on the first surface of the base layer, wherein:
      the indicator comprises a first marking configured to indicate from the first surface the position of the adhesive layer on the second surface; and the indicator comprises a second marking configured to indicate how to use the defibrillator hair removal pad, wherein the base layer has a perimeter comprising outermost edges completely around the base layer and wherein the adhesive layer extends partly widthwise respective to the width of the second surface of the base layer such that the base layer comprises a second exposed portion of the second surface between each edge of the adhesive layer and an adjacent edge of the second surface such that there is a continuous exposed surface completely around the perimeter of the second surface, the method comprising:

positioning the adhesive layer on the body hair on the skin of the subject, wherein:
- the adhesive layer is positioned using the first marking of the indicator on the first surface of the base layer to determine the position of the adhesive layer on the second surface of the base layer;

positioning the adhesive layer comprises contacting the second exposed portion of the second surface of the base layer and thereby holding the base layer to thereby position the adhesive layer; and the adhesive layer does not extend to the outermost edges of the base layer for the entire length of the outermost edges and the adhesive layer is positioned such that the adhesive layer is adhered to the body hair by applying contact upon the first surface of the base layer, and the second surface of the base layer adjacent to the outermost edges of the base layer are not adhered to the subject because of the absence of the substance of the adhesive layer on the second surface of the base layer adjacent to the outermost edges of the base layer for the entire length of the outermost edges; and pulling and removing the body hair from the skin by pulling the adhesive layer away from the skin, wherein:
- pulling the adhesive layer comprises contacting the first exposed portion of the second surface of the base layer and thereby holding and pulling the base layer to thereby pull the adhesive layer away from the skin; and
- pulling the adhesive layer further comprises pulling the adhesive layer in a direction indicated by the second marking of the indicator;

wherein positioning the adhesive layer and pulling the adhesive layer is further based on how to use the defibrillator hair removal pad indicated by the second marking of the indicator.

* * * * *